(12) United States Patent
Theberge et al.

(10) Patent No.: US 11,090,651 B2
(45) Date of Patent: Aug. 17, 2021

(54) FLUIDIC PATTERNING OF HYDROGEL PARTITIONS

(71) Applicant: University of Washington, Seattle, WA (US)

(72) Inventors: Ashleigh Theberge, Seattle, WA (US); Erwin Berthier, Seattle, WA (US); Ilham Wilson, Seattle, WA (US); John Day, Seattle, WA (US); Tianzi Zhang, Seattle, WA (US); Ulri Lee, Seattle, WA (US)

(73) Assignee: University of Washington, Seattle, WA (US)

( * ) Notice: Subject to any disclaimer, the term of this patent is extended or adjusted under 35 U.S.C. 154(b) by 278 days.

(21) Appl. No.: 16/428,829

(22) Filed: May 31, 2019

(65) Prior Publication Data

US 2019/0366334 A1     Dec. 5, 2019

Related U.S. Application Data

(60) Provisional application No. 62/678,908, filed on May 31, 2018.

(51) Int. Cl.
*B01L 3/00* (2006.01)
*C12M 3/06* (2006.01)

(52) U.S. Cl.
CPC ....... *B01L 3/502707* (2013.01); *C12M 23/16* (2013.01); *B01L 2200/12* (2013.01);
(Continued)

(58) Field of Classification Search
CPC ... C12M 23/16; C12M 25/14; B01L 2200/12; B01L 2300/0829; B01L 2300/0864;
(Continued)

(56) References Cited

U.S. PATENT DOCUMENTS

2003/0215941 A1   11/2003   Campbell
2011/0091930 A1   4/2011   Vacanti
(Continued)

FOREIGN PATENT DOCUMENTS

WO   2015084168 A1   6/2015

OTHER PUBLICATIONS

L. Goers, P. Freemont and K. M. Polizzi, Co-culture systems and technologies: taking synthetic biology to the next level, J. R. Soc., Interface, 2014, 11, 0065.
(Continued)

*Primary Examiner* — Jennifer Wecker
(74) *Attorney, Agent, or Firm* — Perkins Coie LLP

(57) ABSTRACT

The present technology provides spontaneous capillary flow devices for patterning walls on a hydrophilic substrate. In some embodiments, the devices include rails having a first end portion for receiving a flowable material, a second end portion opposite the first end portion, and a base portion having a flow surface extending between the first end portion and the second end portion. The flow surface can face the hydrophilic substrate and define a flow path. When the flowable material is released into the first end portion, the flowable material flows via spontaneous capillary flow from the first end portion to the second end portion along the flow path to create a partition on the hydrophilic substrate.

19 Claims, 24 Drawing Sheets

(52) U.S. Cl.
CPC . *B01L 2300/0864* (2013.01); *B01L 2300/123* (2013.01); *B01L 2300/163* (2013.01); *B01L 2400/0406* (2013.01)

(58) Field of Classification Search
CPC ......... B01L 2300/123; B01L 2300/163; B01L 2400/0406; B01L 3/502707; B01L 3/5085
See application file for complete search history.

(56) References Cited

U.S. PATENT DOCUMENTS

| | | | |
|---|---|---|---|
| 2011/0212501 | A1 | 9/2011 | Yoo |
| 2015/0079668 | A1* | 3/2015 | Kobayashi ........... G01N 33/558 435/287.2 |
| 2015/0276562 | A1 | 10/2015 | Fraden |
| 2015/0293073 | A1 | 10/2015 | Murphy |
| 2016/0369221 | A1 | 12/2016 | Ponomarenko |
| 2017/0355945 | A1 | 12/2017 | Kamm |
| 2019/0321819 | A1* | 10/2019 | Arango ............. B01L 3/502738 |

OTHER PUBLICATIONS

D. R. Bogdanowicz and H. H. Lu, Studying cell-cell communication in co-culture, Biotechnol. J., 2013, 8(4), 395-396.
V. V. Abhyankar and D. J. Beebe, Spatiotemporal micropatterning of cells on arbitrary substrates, Anal. Chem., 2007, 79, 4066-4073.
S. N. Bhatia, U. J. Balis, M. L. Yarmush and M. Toner, Microfabrication of hepatocyte/fibroblast co-cultures: Role of homotypic cell interactions, Biotechnol. Prog., 1998, 14(3), 378-387.
H. J. Kim, J. Q. Boedicker, J. W. Choi and R. F. Ismagilov, Defined spatial structure stabilizes a synthetic multispecies bacterial community, Proc. Natl. Acad. Sci. U. S. A., 2008, 105, 18188-18193.
Y. Miki, K. Ono, S. Hata, T. Suzuki, H. Kumamoto and H. Sasano, The advantages of co-culture over mono cell culture in simulating in vivo environment, J. Steroid Biochem. Mol. Biol., 2012, 131, 68-75.
K. Hatherell, P. O. Gouraud, I. A. Romero, B. Weksler and G. J. Pilkington, Development of a three-dimensional, all-human in vitro model of the blood-brain barrier using mono-, co-, and tri-cultivation Transwell models, J. Neurosci. Methods, 2011, 199, 223-229.
D. A. Lauffenburger and S. H. Zigmond, Chemotactic factor concentration gradients in chemotaxis assay systems, J. Immunol. Methods, 1981, 40, 45-60.
T. M. Keenan and A. Folch, Biomolecular gradients in cell culture systems, Lab Chip, 2008, 8, 34-57.
A. D. Gracz, I. A. Williamson, K. C. Roche, M. J. Johnston, F. Wang, Y. Wang, P. J. Attayek, J. Balowski, X. F. Liu, R. J. Laurenza, L. T. Gaynor, C. E. Sims, J. A. Galanko, L. Li, N. L. Allbritton and S. T. Magness, A high-throughput platform for stem cell niche co-cultures and downstream gene expression analysis, Nat. Cell Biol., 2015, 17, 340-349.
L. M. Borland, S. Kottegoda, K. S. Phillips and N. L. Allbritton, Chemical analysis of single cells, Annu. Rev. Anal. Chem., 2008, 1, 191-227.
S. N. Bhatia and D. E. Ingber, Nat. Biotechnol., 2014, 32, 760-772.
S. March, V. Ramanan, K. Trehan, S. Ng, A. Galstain and N. Gural, et al., Micropatterned coculture of primary human hepatocytes and supportive cells for the study of hepatotropic pathogens, Nat. Protoc., 2015, 10, 2027-2053.
S. Takayama, J. C. McDonald, E. Ostuni, M. N. Liang, P. J. Kenis, R. F. Ismagilov and G. M. Whitesides, Patterning Cells and Their Environments Using Multiple Laminar Fluid Flows in Capillary Networks, Proc. Natl. Acad. Sci. U. S. A., 1999, 96, 5545-5548.
T. Kojima, C. Moraes, S. P. Cavnar, G. D. Luker and S. Takayama, Surface-templated hydrogel patterns prompt matrix-dependent migration of breast cancer cells towards chemokine-secreting cells, Acta Biomater., 2015, 13, 68-77.

A. P. Wong, R. Perez-Castillejos, J. C. Love and G. M. Whitesides, Partitioning microfluidic channels with hydrogel to construct tunable 3-D cellular microenvironments, Biomaterials, 2008, 29, 1853-1861.
C. Y. Li, K. R. Stevens, R. E. Schwartz, B. S. Alejandro, J. H. Huang and S. N. Bhatia, Micropatterned cell-cell interactions enable functional encapsulation of primary hepatocytes in hydrogel microtissues, Tissue Eng., Part A, 2014, 20(15-16), 2200-2212.
E. W. K. Young, C. Pak, B. S. Kahl, D. T. Yang, N. S. Callander, S. Miyamoto and D. J. Beebe, Microscale functional cytomics for studying hematologic cancers, Blood, 2012, 119, e76-e85.
Y. Torisawa, B. Mosadegh, G. D. Luker, M. Morell, K. S. O'Shea and S. Takayama, Microfluidics hydrodynamic cellular patterning for systematic formation of co-culture spheroids, Integr. Biol., 2009, 1, 649-654.
P. Gheibi, K. J. Son, G. Stybayeva and A. Revzin, Harnessing endogenous signals from hepatocytes using a low volume multiwell plate, Integr. Biol., 2017, 9, 427.
C. J. Flaim, S. Chien and S. N. Bhatia, An extracellular matrix microarray for probing cellular differentiation, Nat. Methods, 2005, 2, 119-125.
C. P. Huang, J. Lu, H. Seon, A. P. Lee, L. A. Flanagan, H. Y. Kim, A. J. Putnam and N. L. Jeon, Engineering microscale cellular niches for three-dimensional multicellular co-cultures, Lab Chip, 2009, 9, 1740-1748.
Y. S. Torisawa, B. Mosadegh, S. P. Cavnar, M. Ho and S. Takayama, Transwells with microstamped membranes produce micropatterned two-dimensional and three-dimensional co-cultures, Tissue Eng., Part C, 2011, 17(1), 61-67.
M. Domenech, H. Yu, J. Warrick, N. M. Badders, I. Meyvantsson, C. M. Alexander and D. J. Beebe, Cellular observations enabled by microculture: paracrine signaling and population demographics, Integr. Biol., 2009, 1, 267-274.
L. J. Barkal, A. B. Theberge, C. J. Guo, J. Spraker, L. Rappert and J. Berthier, et al., Microbial metabolomics in open microscale platforms, Nat. Commun., 2016, 7, 10610.
C. M. Carney, J. L. Muszynski, L. N. Strotman, S. R. Lewis, R. L. O'Connell, D. J. Beebe, A. B. Theberge and J. S. Jorgenson, Cellular microenvironment dictates androgen production by murine fetal Leydig cells in primary culture, Biol. Reprod., 2014, 91(4), 85.
E. E. Hui and S. N. Bhatia, Micromechanicai control of cell-cell interactions, Proc. Natl. Acad. Sci. U. S. A., 2007, 104, 5722-5726.
S. H. Lee, A. J. Heinz, S. Shin, Y. G. Jung, S. E. Choi, W. Park, J. H. Roe and S. Kwon, Capillary based patterning of cellular communities in laterally open channels, Anal. Chem., 2010, 82, 2900-2906.
S. Bersini, J. S. Jeon, G. Dubini, C. Arrigoni, S. Chung and J. L. Charest, et al., A microfluidic 3D in vitro model for specificity of breast cancer metastasis to bone, Biomaterials, 2014, 35, 2454-2461.
Y. Gao, D. Majumdar, B. Jovanovic, C. Shaifer, P. C. Lin and A. Zijlstra, et al., A versatile valve-enabled microfluidic cell co-culture platform and demonstration of its applications to neurobiology and cancer biology, Biomed. Microdevices, 2011, 13, 539-548.
K. J. Son, P. Gheibi, G. Stybayeva, A. Rahimian and A. Revzin, Detecting cell-secreted growth factors in microfluidic devices using bead-based biosensors, Microsyst. Nanoeng., 2017, 3, 17025.
D. Patel, Y. Geo, K. Son, C. Siltanen, R. M. Neve, K. Ferrara and A. Revzin, Microfluidic co-cultures with hydrogel-based ligand trap to study paracrine signals giving rise to cancer drug resistance, Lab Chip, 2015, 15, 4614.
K. J. Regehr, M. Domenech, J. T. Koepsel, K. C. Carver, S. J. Ellison-Zelski, W. L. Murphy, L. A. Schuler, E. T. Alarid and D. J. Beebe, Biological implications of polydimethylsiloxane-based microfluidic cell culture, Lab Chip, 2009, 9(15), 2132-2139.
J. N. Lee, C. Park and G. M. Whitesides, Solvent compatibility of poly(dimethylsiloxane)-based microfluidic devices, Anal. Chem., 2003, 75(23), 6544-6554.
E. Berthier, E. W. Young and D. J. Beebe, Engineers are from PDMS-land, biologists are from polystyrenia, Lab Chip, 2012, 12(7), 1224-1237.

(56) References Cited

OTHER PUBLICATIONS

B. P. Casavant, E. Berthier, A. B. Theberge, J. Berthier, S. I. Montanez-Sauri and L. L. Bischel, et al., Suspended Microfluidics, Proc. Natl. Acad. Sci. U. S. A., 2016, 110, 10111-10116.

J. Berthier, K. A. Brakke and E. Berthier, Theory of spontaneous capillary flows. In: Open Microfluidics, Wiley, 2016.

A. K. Au, W. Lee and A. Folch, Mail-order microfluidics: evaluation of stereolithography for the production of microfluidic devices, Lab Chip, 2014, 14, 1294.

A. K. Au, W. Huynh, L. F. Horowitz and A. Folch, 3D-Printed Microfluidics, Angew. Chem., Int. Ed., 2016, 55, 3862-3881.

O. E. Franco, M. Jiang, D. W. Strand, J. Peacock, S. Fernandez and R. S. Jackson II, et al., Altered TGF-β Signaling in a Subpopulation of Human Stromal Cells Promotes Prostatic Carcinogenesis, Cancer Res., 2011, 71(4), 1272-1281.

D. R. Church, E. Lee, T. A. Thompson, H. S. Basu, M. O. Ripple, E. A. Ariazi and G. Wilding, Induction of AP-1 Activity by Androgen Activation of the Androgen Receptor in LNCaP Human Prostate Carinoma Cells, Prostate, 2005, 63, 155-168.

K. Shimizu and N. P. Keller, Genetic involvement of a cAMP-dependent protein kinase in a G protein signaling pathway regulating morphological and chemical transitions in Aspergillus nidulans, Genetics, 2001, 157, 591-600.

M. Verhulsei, M. Vignes, S. Descroix, L. Malaquin, D. M. Vignjevic and J. L. Viovy, A review of microfabrication and hydrogel engineering for micro-organs on chips, Biomaterials, 2014, 35, 1816-1832.

P. Concus and R. Finn, On the behavior of a capillary surface in a wedge, Proc. Natl. Acad. Sci. U. S. A., 1969, 2(63), 292-299.

M. S. Liberio, M. C. Sadowski, C. Soekmadji, R. A. Davis and C. C. Nelson, Differential effects of tissue culture coating substrates on prostate cancer cell adherence, morphology, and behavior, PLoS One, 2014, 9(11), e112122.

Corning® PureCoat™ Cultureware, Corning Data Sheet CLSDL-CC-046 REV1, 2013. Web. https://www.corning.com/media/worldwide/cls/documents/CLS-DL-CC-046_REV1.pdf.

N. Bhattacharjee, A. Urrios, S. Kang and A. Folch, The upcoming 3D-printing revolution in microfluidics, Lab Chip, 2016, 16, 1720.

S. Saegusa, M. Totsuka, S. Kaminogawa and T. Hosoi, *Saccharomyces cerevisiae* and Candida albicans stimulate cytokine secretion from human neutrophil-like HL-60 cells differentiated with retinoic acid or dimethylsulfoxide, Biosci., Biotechnol., Biochem., 2009, 73(12), 2600-2608.

R. Hatoum, S. Labrie and I. Fliss, Antimicrobial and probiotic properties of yeasts: from fundamental to novel applications, Front. Microbiol., 2012, 3, 421.

G. B. Huffnagle and M. C. Noverr, The emerging world of the fungal microbiome, Trends Microbiol., 2013, 7(21), 334-341.

The Human Microbiome Project Consortium, Structure, function, and diversity of the healthy human microbiome, Nature, 2012, 486, 207-214.

L. J. Barkal, C. L. Procknow, Y. R. Álvarez-Garcia, M. Niu, J. A. Jiménez-Torres and R. A. Brockman-Schneider, et al., Microbial volatile communication in human organotypic lung models, Nat. Commun., 8: 1770 (2017).

L. J. Barkal, E. Berthier, A. B. Theberge, N. P. Keller and D. J. Beebe, Multikingdom microscale models, PLoS Pathog., 2017, 13(8), e1006424.

K. H. Spencer, M. Y. Kim, C. C. W. Hughes and E. E. Hui, A screen for short-range paracrine interactions, Integr. Biol., 2014, 6, 382.

N. Rao, G. N. Grover, L. G. Vincent, S. C. Evans, Y. S. Choi, K. H. Spencer, E. E. Hui, A. J. Engler and K. L. Christman, A co-culture device with a tunable stiffness to understand combinatorial cell-cell and cell-matrix interactions, Integr. Biol., 2013, 5, 1344.

K. Smith, R. Rajendran, S. Kerr, D. Lappin, W. G. Mackay, C. Williams and G. Ramage, Aspergillus fumigatus enhances elastase production in Pseudomonas aeruginosa co-cultures, Med. Mycol., 2015, 53, 645-655.

E. Mowat, R. Rajendran, C. Williams, E. McCulloch, B. Jones, S. Lang and G. Ramage, Pseudomonas aeruginosa and their small diffusible extracellular molecules inhibit Aspergillus fumigatus biofilm formation, FEMS Microbiol. Lett., 2010, 313, 96-102.

H. Zheng, J. Kim, M. Liew, J. K. Yan, O. Herrera, J. W. Bok, N. L. Kelleher, N. P. Keller and Y. Wang, Redox metabolites signal polymicrobial biofilm development via the NapA oxidative stress cascade in Aspergillus, Curr. Biol., 2015, 25, 29-37.

Samuel B. Berry, Tianzi Zhang, John H. Day, Xiaojing Su, Ilham Z. Wilson, Erwin Berthier and Ashleigh B. Theberge "Upgrading well plates using open microfluidic patterning" Lab Chip, 2017, 17, 4253.

Samuel B. Berry, Tianzi Zhang, John H. Day, Xiaojing Su, Ilham Z. Wilson, Erwin Berthier and Ashleigh B. Theherge "Upgrading well plates using open microfluidic patterning" Lab Chip, 2017, Electronic Supporting Information.

Torr EE, Ngam CR, Bernau K, Tomasini-Johansson B, Acton B, Sandbo N. J Biol Chem 2015, 290(11):6951-61.

Francesco Piraino, Gulden Camci-Unal, Matthew J. Hancock, Marco Rasponi, and Ali Khademosseini "Multi-gradient hydrogels produced layer by layer with capillary flow and crosslinking in open microchannels" Lab on a Chip 2012 vol. 12 / Issue 3 p. 659-661.

Sharon K. Hamilton, Nathaniel C. Bloodworth, Christopher S. Massad, Taymour M. Hammoudi, Shalu Sun, Peter J. Yang, Hang Lu, and Johnna S. Temenoff "Development of 3-D Hydrogel Culture Systems With On-Demand Cell Separation" Biotechnology Journal 2013 vol. 8 / Issue 4 p. 485-495.

Oliver Lieleg, Katherina Ribbeck "Biological Hydrogels as Selective Diffusion Barriers" Trends in Cell Biology 2011 vol. 21 / Issue 9 p. 543-551.

Shin, Y. et al. Microfluidic assay for simultaneous culture of multiple cell types on surfaces or within hydrogels. Nat. Protoc. (2012).

Gao, B., Konno, T. & Ishihara, K. Building cell-containing multilayered phospholipid polymer hydrogels for controlling the diffusion of a bioactive reagent. RSC Adv. (2015).

Ahearne, M. Introduction to cell-hydrogel mechanosensing. Interface Focus (2014).

\* cited by examiner

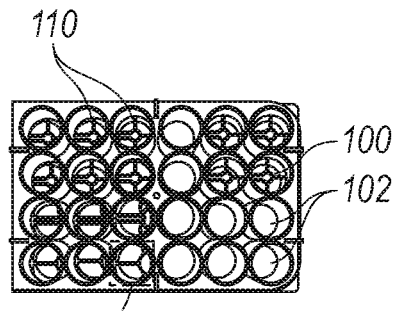
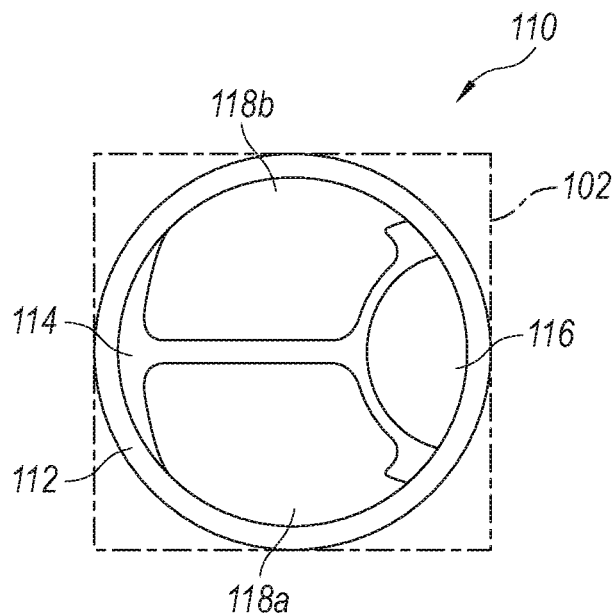
Fig. 1A
Fig. 1B
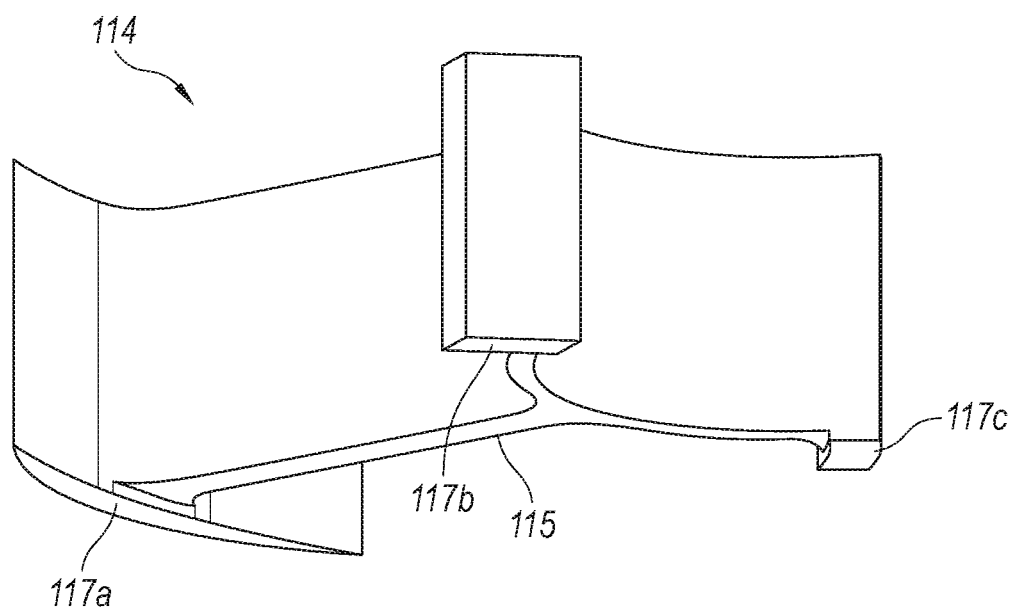
Fig. 1C

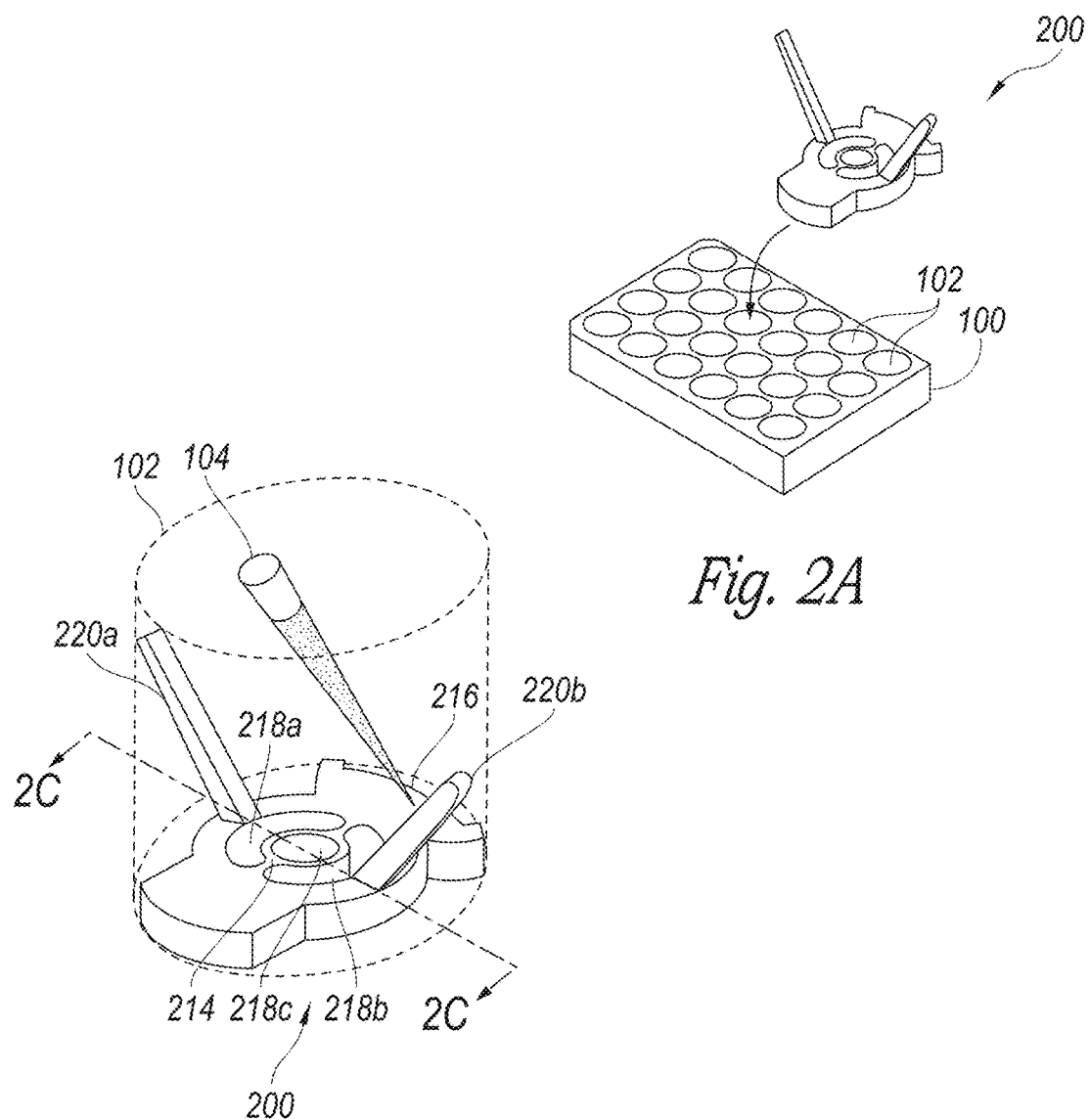
*Fig. 2A*
*Fig. 2B*
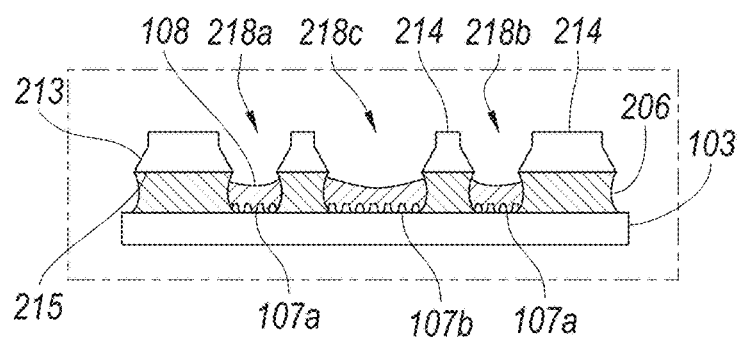
*Fig. 2C*

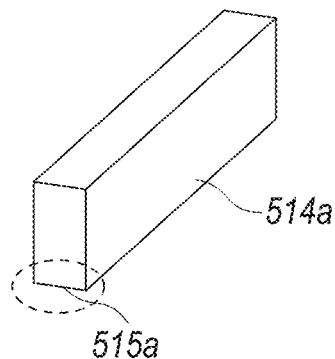
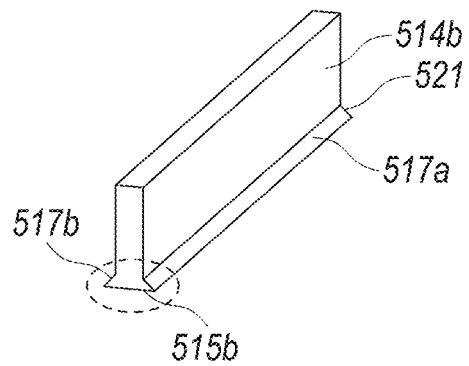
Fig. 5A  Fig. 5B
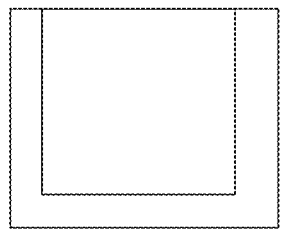
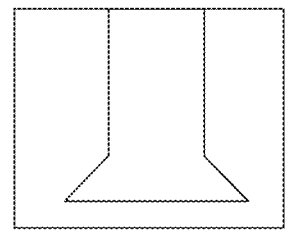
Fig. 5C  Fig. 5D
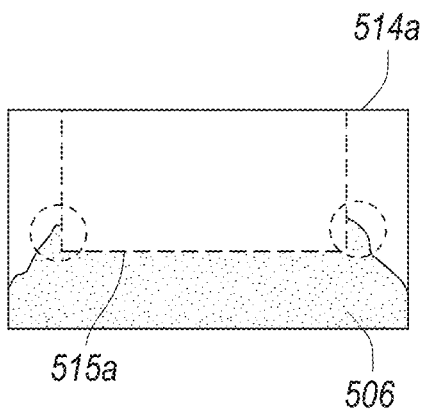
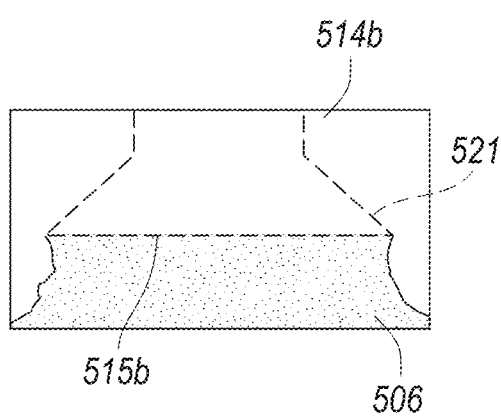
Fig. 5E  Fig. 5F

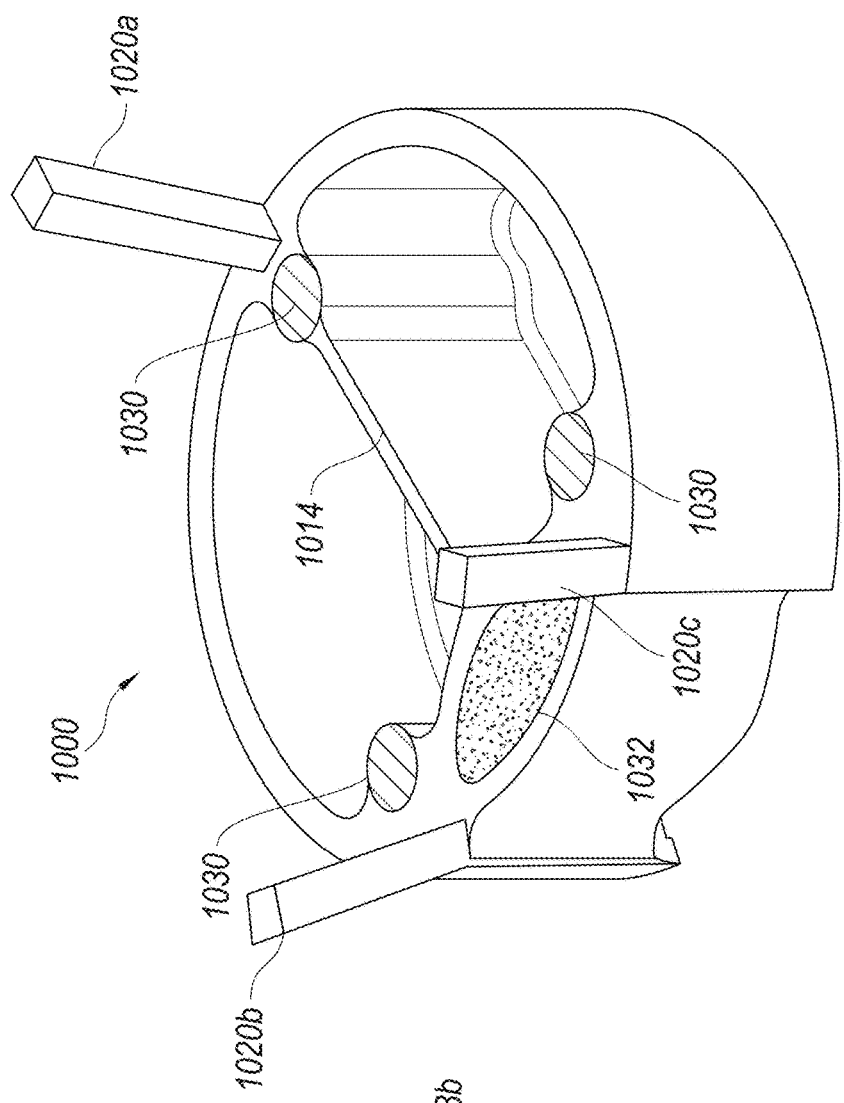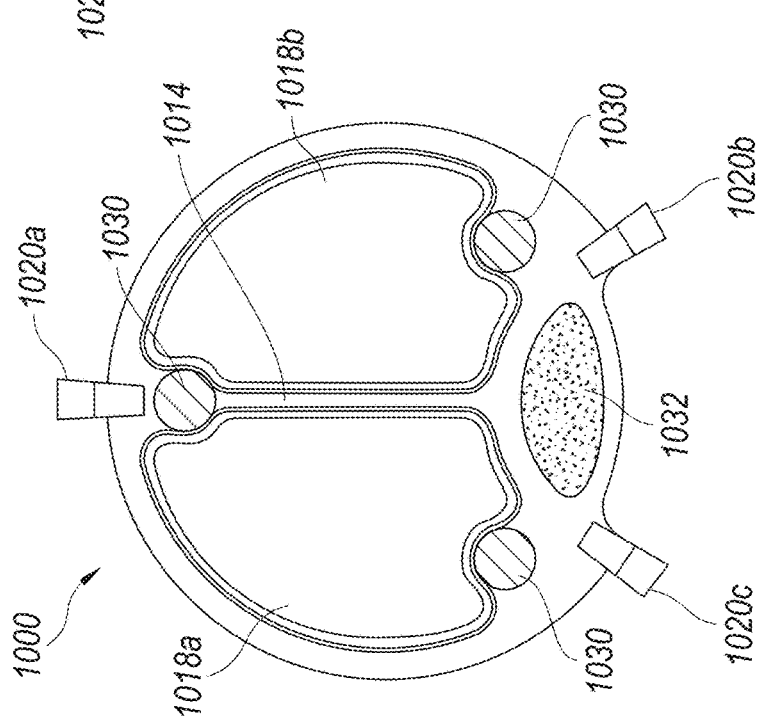

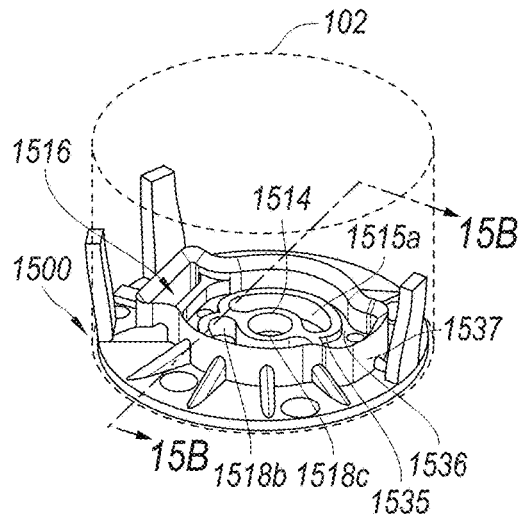
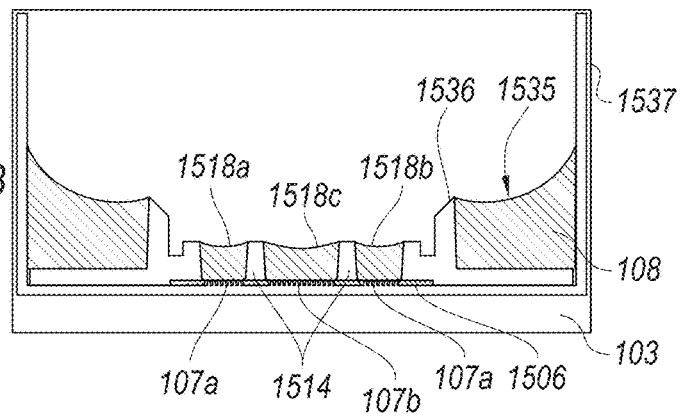
Fig. 15A    Fig. 15B
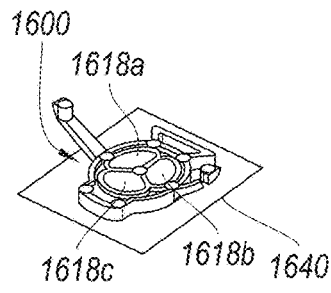
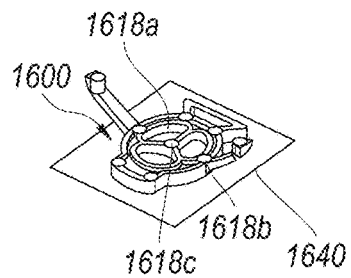
Fig. 16A    Fig. 16B
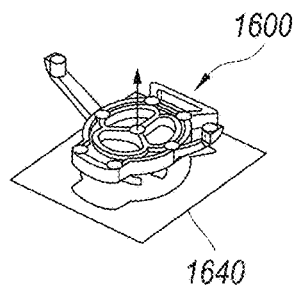
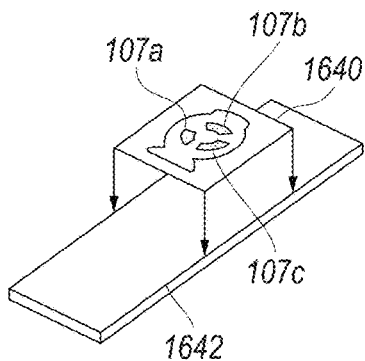
Fig. 16C    Fig. 16D

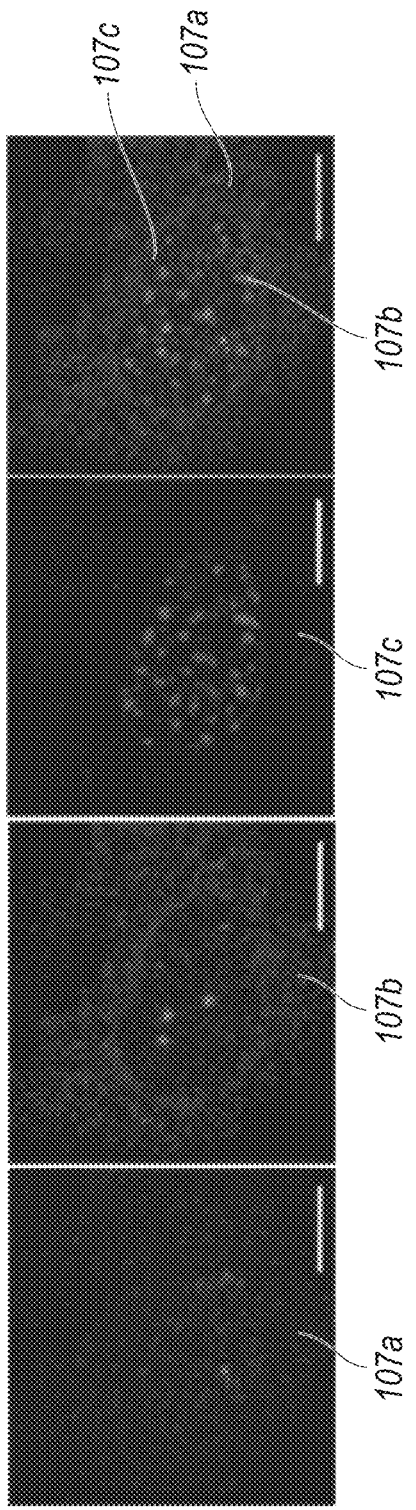
Fig. 17A  Fig. 17B  Fig. 17C  Fig. 17D
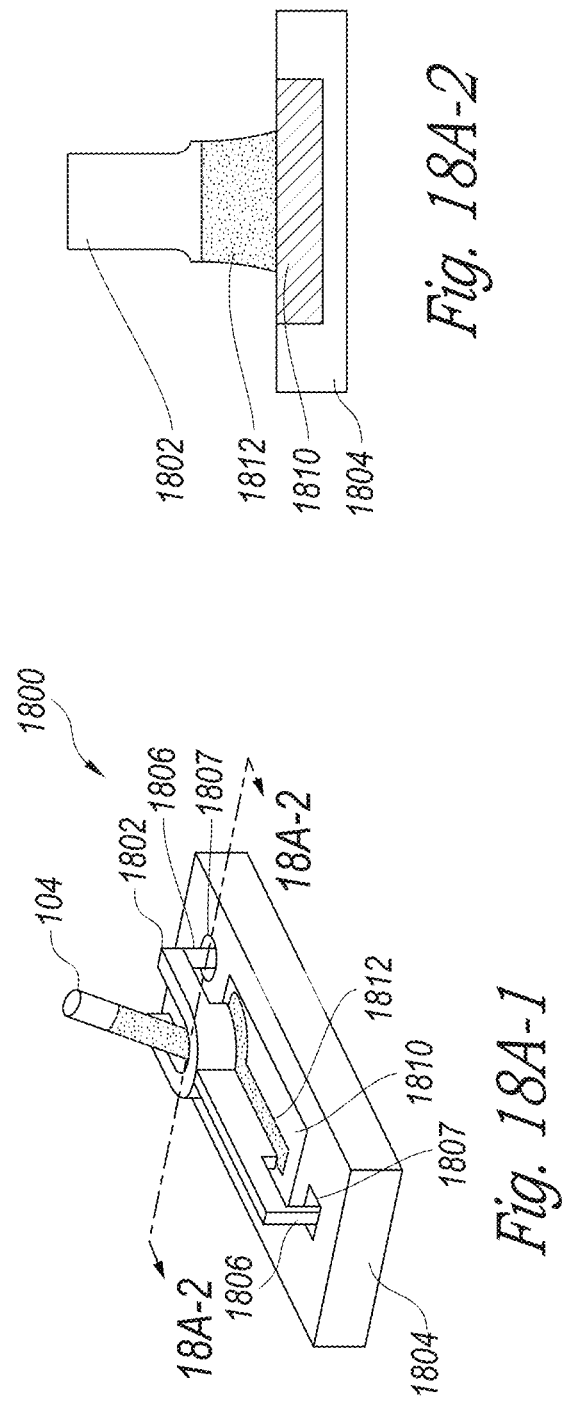
Fig. 18A-1
Fig. 18A-2

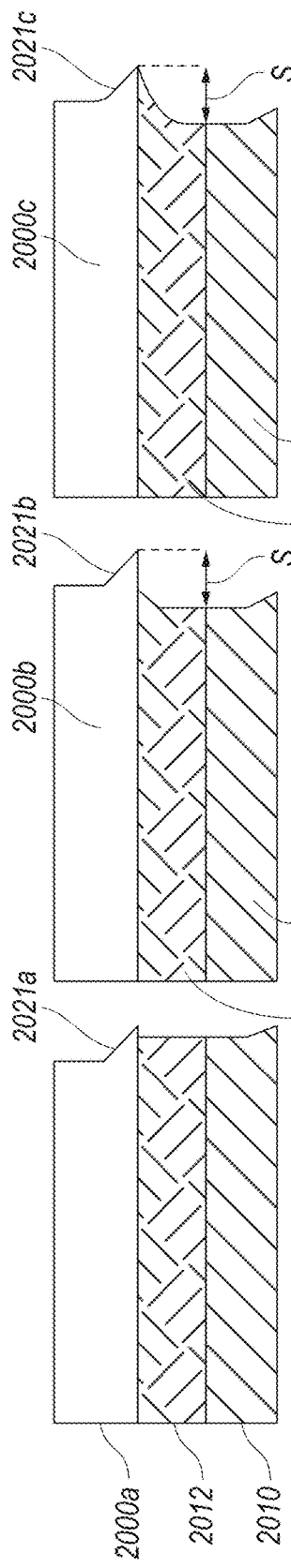
Fig. 20A  Fig. 20B  Fig. 20C
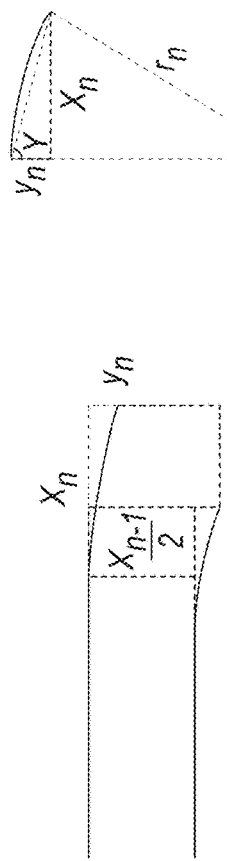
Fig. 21A
Fig. 21B
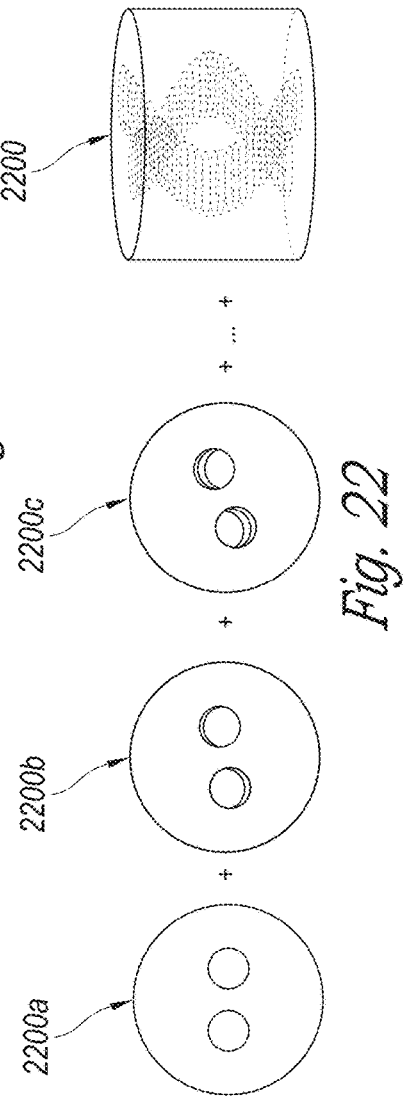
Fig. 22

FLUIDIC PATTERNING OF HYDROGEL PARTITIONS

CROSS-REFERENCE TO RELATED APPLICATION(S)

The present application claims priority to U.S. Provisional Patent Application No. 62/678,908, titled "FLUIDIC PATTERNING OF HYDROGEL PARTITIONS," filed May 31, 2018, the disclosure of which is hereby incorporated by reference in its entirety.

FEDERAL FUNDING STATEMENT

This invention was made with government support under Grant Nos. R01 HD090660 and R35 GM128648, awarded by the National Institutes of Health. The government has certain rights in the invention.

TECHNICAL FIELD

The present technology generally relates to systems, methods, and devices for open microfluidics and, in particular, relates to open microfluidic devices and techniques for creating partitions on cell culture substrates.

BACKGROUND

Modeling soluble factor signaling between human cell types and across cells, bacteria, and fungi advances the study of organ function and disease mechanisms. A powerful approach in modeling this type of signaling utilizes systems that physically separate cell types, yet permit soluble small molecules and proteins to diffuse and perform their signaling mechanism. This can typically be accomplished using engineered systems such as Transwell inserts or innovative microfluidic platforms. Both approaches have been enabling for soluble factor signaling and coculture studies, but are fundamentally limited in that they require specifically engineered systems, limiting their versatility and transferability.

BRIEF DESCRIPTION OF THE DRAWINGS

FIGS. 1A-1E illustrate a first flow device configured in accordance with select embodiments of the present technology.

FIGS. 2A-2G illustrate a second flow device configured in accordance with select embodiments of the present technology.

FIGS. 5A-5F illustrate flow devices with varying rail geometry configured in accordance with select embodiments of the present technology.

FIGS. 10A-10B are illustrations of a flow device having certain features that facilitate device fabrication via injection molding in accordance with select embodiments of the present technology.

FIGS. 13A-1-13G illustrate multikingdom coculture devices and validation studies in accordance with select embodiments of the present technology.

FIG. 15A-15B illustrates a flow device having a reservoir to mitigate evaporation and configured in accordance with select embodiments of the present technology.

FIGS. 16A-16D illustrate a workflow for culturing cells on a glass cover slide using flow devices to facilitate high resolution microscopy in accordance with select embodiments of the present technology.

FIGS. 17A-17D are images of cells cultured using the workflow depicted in FIGS. 16A-16D in accordance with select embodiments of the present technology.

FIGS. 18A-1-18B illustrate a flow device for layer-by-layer fabrication of a three-dimensional structure in accordance with select embodiments of the present technology.

FIGS. 20A-20C illustrate techniques for creating an overhanging structure in a three-dimensional structure in accordance with select embodiments of the present technology.

FIGS. 21A-21B are schematic illustrations depicting certain device parameters used to determine the schematics of devices used to create overhang features in a three-dimensional structure in accordance with select embodiments of the present technology.

FIG. 22 illustrates a complex, multi-layered three-dimensional structure fabricated using layer-by-layer fabrication methods in accordance with select embodiments of the present technology.

DETAILED DESCRIPTION

Figure 1D:
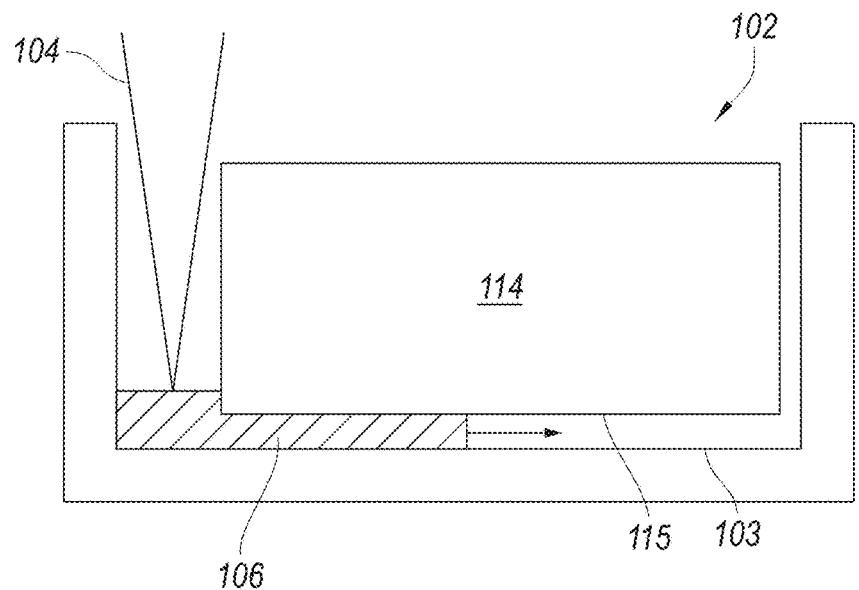

The present technology provides systems, methods, and devices that use open microfluidics to pattern hydrogel walls on cell culture substrates. The devices and methods described herein can be applied to cell culture, cell-based assays, and culture of multiple cell types (i.e., co-culture, tri-culture, multi-culture) for biomedical applications, drug development, toxicity testing, and basic research & development. Specific culture applications include, for example, human/mammalian cells and microbes. The present technology also provides systems, methods, and devices for layer-by-layer fabrication of three-dimensional structures.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the claims but are not described in detail with respect to FIGS. 1A-24B.

Reference throughout this specification to "one embodiment" or "an embodiment" means that a particular feature, structure or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "substantially," "approximately," and "about" are used herein to mean the stated value plus or minus 10%.

The headings provided herein are for convenience only and do not interpret the scope or meaning of the claimed present technology.

Cell Cocultures

Cell cocultures have been used to recapitulate specific aspects of in vivo cellular signaling phenomena, providing insight into complex physiological systems (e.g., organs, immune response, etc.). Specifically, segregated coculture, in which cell types are physically separated but are still able to communicate via diffusion of signaling molecules, can capture dynamic, reciprocal signaling between cell types and isolate the effects of soluble factors from the effects of heterotypic contact that include juxtacrine signaling pathways and cell stimulation. Segregated coculture methods are available as commercial Transwell inserts which integrate with standard culture plates, but are limited by fixed culture configurations, the inability to tune the size of the culture regions, the number of cultures in communication, the use of alternative surface materials (e.g., PC, PET, PTFE), poorly defined diffusion gradients that rapidly decay, and the inability to culture multiple cell types on a single surface.

Alternatively, researchers have turned to custom engineered microfluidic systems for segregated coculture, as these systems can provide precise control over cell culture environments, require fewer cells, and can be tailored to mimic physiological conditions. These engineering approaches have generated effective and creative segregated coculture platforms, using techniques such as hydrogel patterning and laminar flow patterning for precise cell seeding and microchannel systems for the isolation of soluble factor effects in complex cocultures. For example, custom engineered microfluidic systems include a reconfigurable, interdigitated coculture system that permits precise temporal and spatial manipulation of coculture, a micro-molded polydimethylsiloxane (PDMS) device that utilizes flow along a rail to pattern gels and selectively seed cells and microbes, hydrogel-based barriers that selectively manipulate the chemical and temporal signaling of cell types in coculture, and a dual-chambered polystyrene (PS) microfluidic device that allows transport of signaling molecules through diffusion channels connecting the segregated chambers. These examples remain limited. For example, many of these approaches use PDMS, which absorbs small molecules, while others use enclosed culture chambers, which are only accessible from the inlet/outlet ports. Moreover, these systems are not compatible with unmodified commercially available tissue-culture surfaces. Thus, despite the push towards simplifying complex cocultures with these engineered systems, integration of custom microsystems with established cultureware remains difficult. Commercially available well plates and tissue culture treated (TCT) surfaces are easy to handle and use, have been validated through decades of experimentation, and are familiar to biological laboratories. Further, production of cell culture-treated surfaces is a technically challenging and labor-intensive process that has been optimized by industry through decades of effort. Therefore, there exists a need for an easy-to-use tool that provides investigators with the flexibility to upgrade their model with multiple cell types while maintaining optimized experimental materials and methods.

The present technology includes segregated coculture technology that can integrate with established cell culture methods and enable the partitioning of cell-culture surfaces in commercially available well plates. For example, certain embodiments of the present technology provide devices that direct the flow of biocompatible hydrogels to create hydrogel walls. The devices can upgrade simple monoculture assays by adding any number of additional cell-culture wells in controlled configurations on the same plane. In some embodiments, the present technology utilizes spontaneous capillary flow (SCF) along an open microfluidic channel comprising a 'rail' insert (channel ceiling), a cell culture substrate surface (channel floor), and two open air interfaces (channel sides). This type of flow allows the easy patterning of hydrogel and its polymerization, thereby creating permeable cell culture regions. In some embodiments, the incorporation of SCF as the mechanism of flow can eliminate the need for external pumping systems during the hydrogel wall fabrication process.

In some embodiments, the devices can be insertable into individual wells and easy to use, as gels and cells can be applied in open wells by simple pipetting. The accessibility to cell culture areas provides several advantages; for example, the open chambers and channels demarcated by the hydrogel walls do not have a ceiling and as such are pipette accessible from the top. Thus, cell seeding, media changing, reagent addition, and the removal of media for endpoint analysis (e.g., enzyme-linked immunosorbent assay (ELISA), liquid chromatography-mass spectrometry (LC-MS)) can all be achieved by pipetting directly into the culture regions from the top, just as in a traditional well plate. Additionally, the use of open microfluidics enables straightforward rapid prototyping via 3D printing for platform design and injection molding for scale-up and reproducible use in biology research environments. Moreover, the present technology is compatible with multiple different surfaces and can be used for a variety of applications, including, for example, multikingdom coculture, small molecule diffusion, and surface-sensitive cell culture.

The hydrogels used with the present technology can also be modified. For example, entities such as molecules or cells can be added to the hydrogel so that they are embedded in the partitions created with the flow devices described in greater detail below. Thus, in some embodiments, the partitions created can be "active" rather than "passive." In some embodiments, cells can be seeded into the wall and used as indicators in an assay or secretors to prime other cells that are seeded on the substrate surface. In some embodiments, indicator molecules, such as a fluorogenic substrate could be added to the wall such that the wall fluoresces only when cells produce a particular factor. In some embodiments, Antibodies could be added to the wall so that the wall selectively filters out (traps) specific molecules secreted by cells on one side of the wall, preventing them from reaching cells on the other side of the wall.

Select Embodiments of Flow Devices

The present technology provides systems, devices, and methods for patterning hydrogel walls on a cell culture substrate. In some embodiments, the devices are well plate inserts for establishing segregated cell culture zones within a well. FIGS. 1A-1E, for example, illustrate a flow device 110 configured in accordance with select embodiments of the present technology. FIG. 1A illustrates a well plate 100 having a plurality of wells 102. While the well plate 100 is illustrated as a 24-well plate, one skilled in the art will appreciate that the present technology can be utilized with other sizes of well plates. FIG. 1A further illustrates a plurality of flow devices 110 inserted into the plurality of wells (e.g., as "well plate inserts"). FIG. 1B is an enlarged view of an individual flow device 110. The flow device 110 includes an outer perimeter 112, a rail 114, and an inlet 116. When inserted into the well plate 100 (FIG. 1A), the flow device 110 defines a first cell seeding area 118a and a second cell seeding area 118b.

FIG. 1C is an isometric view of the rail 114 before installation with the flow device 10. The rail 114 includes a flow surface 115. The rail 114 further includes a plurality of supports 117a-c. The supports 117a-c are configured to support the device 110 on a cell culture substrate (e.g., a base of a well) and space apart the flow surface 115 and the cell culture substrate to define a flow path. As will be described in greater detail below, when a flow material is inserted into the inlet 116, the flow material flows along the flow path defined by the flow surface 115.

FIG. 1D is a schematic illustration of a workflow when the device 110 is inserted into the well 102. For example, FIG. 1D illustrates a rail 114 positioned within a well 102 such that the flow surface 115 of the rail 114 is spaced apart from the well base 103 (e.g., by the supports 117a-c, not shown). FIG. 1D further illustrates a pipette 104 delivering a flowable material 106 at a first end portion of the rail 114. The flowable material 106 flows along the flow path defined between the flow surface 115 and the well base 103 via spontaneous capillary flow. As will be described in greater detail below, the flow surface 115 defines a top flow surface and the well base 103 defines a bottom flow surface. The device does not require side flow surfaces. Rather, the flow surface 115 controls the flow of the flowable material 106 via pinning the flowable material and promoting spontaneous capillary flow along its length.

Figure 1E:
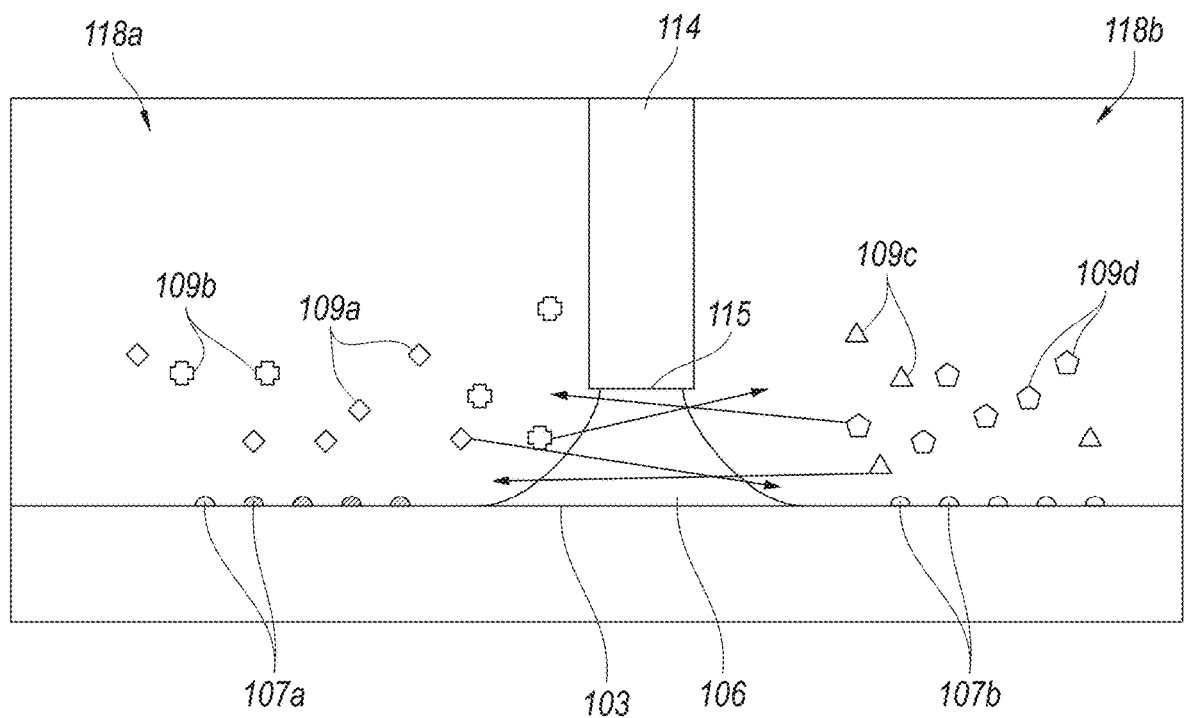

FIG. 1E is a cross-sectional view of the rail 114 positioned within the well 102 following flow of the flowable material 106, polymerization of the flowable material 106, and cell culturing. As illustrated, the flowable material 106 extends between the flow surface 115 of the rail 114 and the well base 103. Once polymerized, the flowable material 106 can create a barrier between a first cell seeding area 118a and a second cell seeding area 118b (collectively referred to as "cell seeding areas 118"). The first cell seeding area 118a can contain a plurality of first seeded cells 107a and the second cell seeding area 118b can contain a plurality of second seeded cells 107b. The cell seeding areas 118 can include a cell culture media (not shown). The polymerized flowable material 106 forming a partition between the cell seeding areas 118 can prevent cells 107a from migrating from the first cell seeding area 118a to the second cell seeding area 118b, and can prevent cells 107b from migrating from the second cell seeding area 118b to the first cell seeding area 118a. However, the flowable material 106 can allow small molecules 109a-d (e.g., signaling molecules) to diffuse through the polymerized flowable material to travel between cell seeding areas 118.

Figure 2D:
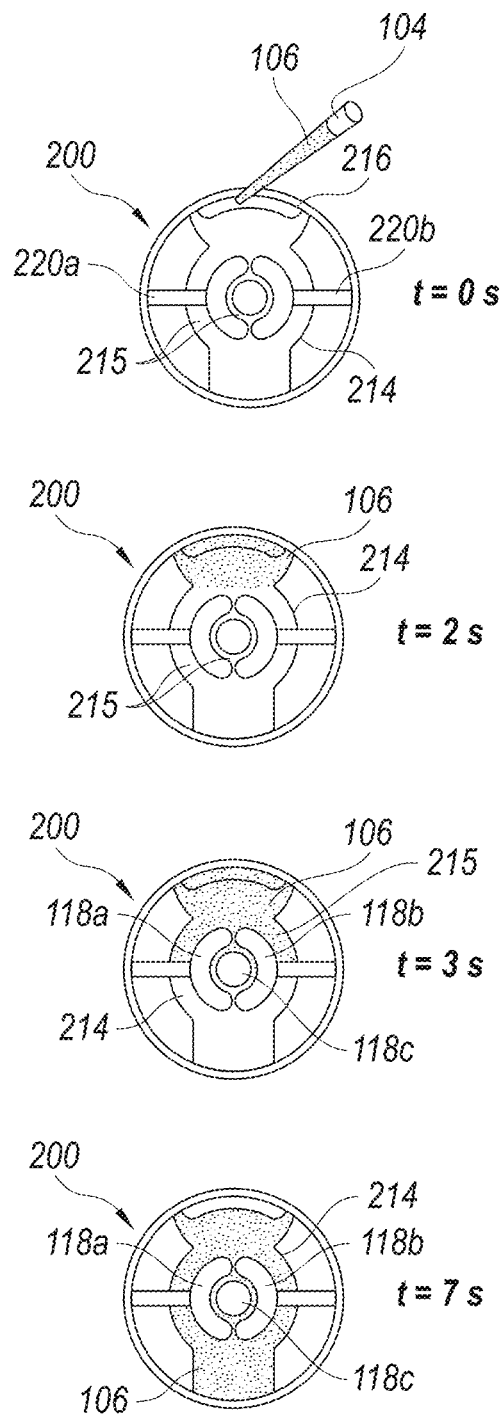

FIGS. 2A-2D illustrate a flow device 200 configured in accordance with select embodiments of the present technology. FIG. 2A, for example, illustrates the flow device 200 above a well plate 100 including a plurality of wells 102. The flow device 200 is sized and shaped to fit into a single well 102 to facilitate partitioning of the well 102 through creation of one or more hydrogel walls. FIG. 2B illustrates the flow device 200 in more detail. More specifically, FIG. 2B illustrates the flow device 200 positioned within a well 102 (defined by dashed lines). The flow device 200 includes an inlet 216, a rail 214, a first support 220a, and a second support 220b (collectively referred to as the "supports 220"). As illustrated in the cross-sectional view of the flow device 200 in FIG. 2C, the rail 214 includes a base portion 213 having a flow surface 215. The flow surface 215 dictates where the hydrogel flows, and thus dictates the patterning of the hydrogel walls 206. Accordingly, the device in FIG. 2B can create a first cell seeding area 218a, a second cell seeding area 218b, and a third cell seeding area 218c (collectively referred to as the "cell seeding areas 218"). As illustrated in the cross-sectional view of the flow device 200 in FIG. 2C, the first cell seeding area 218a, the second cell seeding area 218b, and the third cell seeding are 218c are segregated and can each be cultured with different cells. In the illustrated embodiment, the first cell seeding area 218a and the second cell seeding are 218b are cultured with a first cell type 107a and the third cell seeding area 218c is cultured with a second cell type 107b. One skilled in the art will recognize, however, that three different cell types could be cultured in the cell seeding areas 218. The cell seeding areas 218 can further be filled with a media 108 to promote cell growth and/or viability. FIG. 2B further illustrates a pipette 104 delivering the hydrogel to the inlet 216.

FIG. 2D is a bottom view of hydrogel loading and hydrogel flow at select time points following hydrogel loading. At t=0s, hydrogel 106 is delivered to the inlet 216 via a pipette 104. At time t=2s, the hydrogel 106 begins to flow along the inlet and towards the flow surface 215 of the rail 214. At t=3s, the hydrogel is flowing along the flow surface 215 between the flow device 200 and the well base 103. At t=7s, the hydrogel has flowed from the inlet 216 along a length of the rail 214 over the substantially the entire flow surface 215. Accordingly, the hydrogel is ready for polymerization to form the hydrogel wall. As one skilled in the art will appreciate, the flow timing will be dependent upon a number of characteristics, including, for example, rail configuration and hydrogel composition. Accordingly, the times provided herein are for illustrative purposes and do not limit the present technology.

Figure 2E:
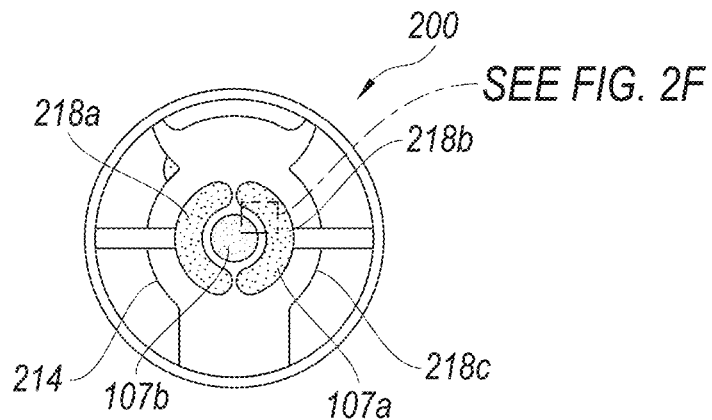
Figure 2F:
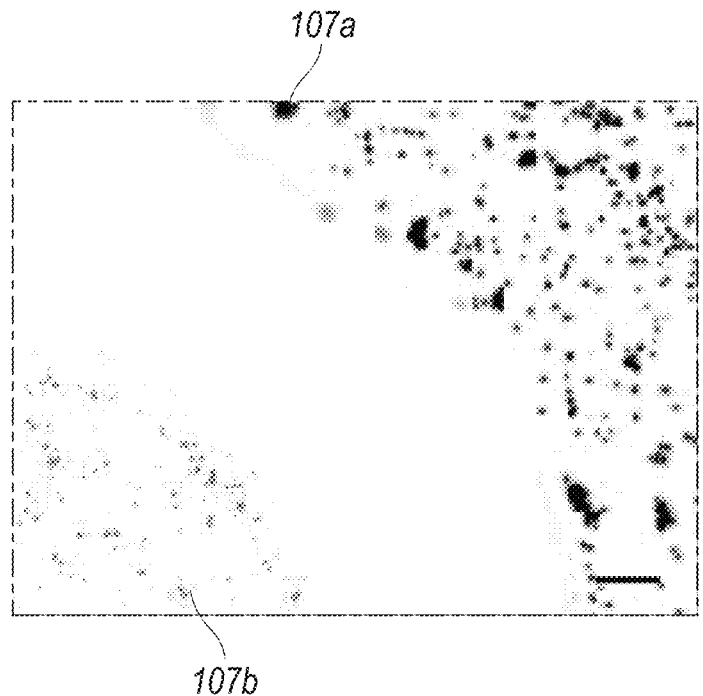

FIGS. 2E and 2F illustrate the integrity of patterned hydrogel walls formed using the flow device 200. The intrinsic characteristics of hydrogels provide several advantages when used for wall fabrication; hydrogels are permeable, thereby enabling diffusion of soluble factors through the wall, yet are able to maintain a defined shape that can act as a physical barrier for objects like cells. These characteristics support the use of hydrogels as a barrier for segregated coculture systems, as they permit soluble factor signaling while prohibiting physical contact between cell types. To demonstrate the segregation and containment of cells by the hydrogel walls, human umbilical arterial smooth muscle cells (HUASMC) cells 107b were stained with CellTracker Red and were selectively seeded into the third cell culture zone 218c, and benign prostate stromal cells (BHPrS) cells 107a were stained with CellTracker Green and were selectively seeded into the first cell seeding area 218a and the second cell seeding area 218b (FIG. 2E). After cell adhesion (e.g., overnight incubation), the cells were imaged at the border of the two culture chambers demonstrating the integrity of the hydrogel wall (image is representative of n=3 devices, scale bar=200 µm). FIG. 2F is an image following cell incubation and adhesions, and demonstrates the physical compartmentalization between the HUASMC cells 107b and the BHPrS cells 107a. Moreover, the device 200 can be used with reduced cell numbers (~2000 cells per chamber), and thus has utility for experiments involving rare or limited cell types (e.g., patient cells).

Figure 2G:
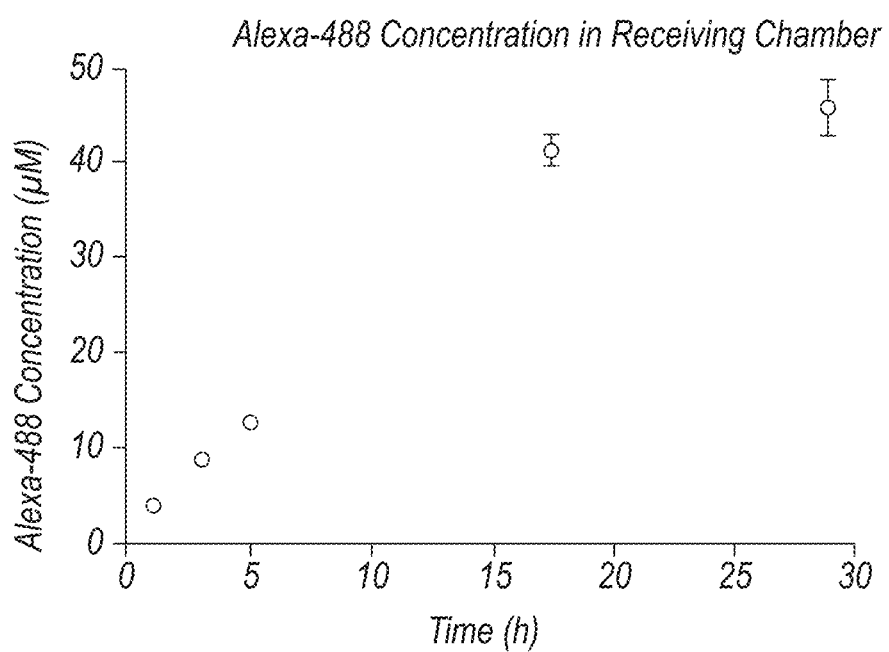

FIG. 2G illustrates the permeability of patterned hydrogel walls to model soluble factor signaling. More specifically, a test small molecule (AlexaFluor-488) was loaded into a first cell culture zone 218a. The concentration of the test small molecule was then measured in the third cell culture zone 218c at various times, and the fluorescence intensity of each sample was measured. FIG. 2G is a graph of the concentration in the third cell culture zone 218c of the test small molecule versus time, and demonstrates an increase in concentration of the test small molecule in the third cell culture zone 218c as time progresses. Moreover, the concentration of AlexaFluor-488 followed the model predicted by the quasi-static Fick law indicating a linear diffusion gradient of AlexaFluor-488 across the hydrogel wall. The diffusion profile demonstrates predictable and controllable signaling across the hydrogel wall. Diffusion time is dependent upon the size of the molecule, the thickness and permeability of the wall, and the distance between the source and the receiver. Therefore, for applications where different diffusion rates are required, the dimensions of the wall and culture chambers and the concentration/type of hydrogel can be adjusted. Accordingly, these results support the use of this platform as a method to study intercellular communication while maintaining physical separation of cell types.

Figure 3A:
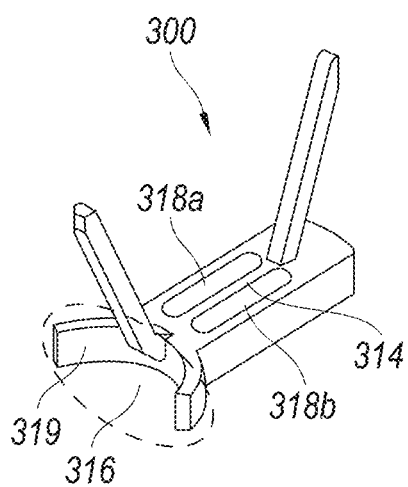
FIGS. 3A-3F illustrate flow devices with and without a controlled inlet and configured in accordance with select embodiments of the present technology.
Figure 3D:
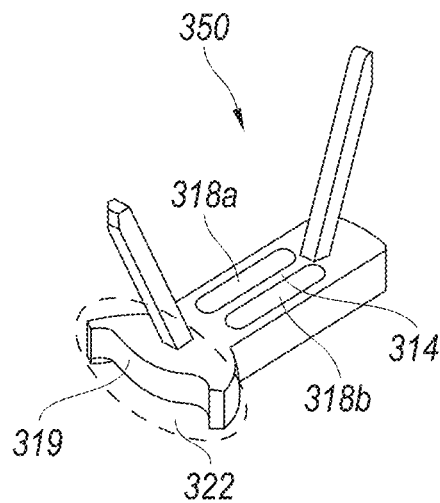
Figure 3B:
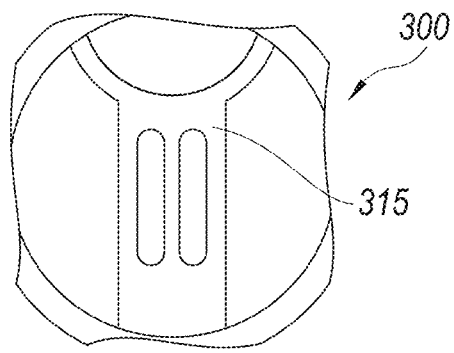
Figure 3E:
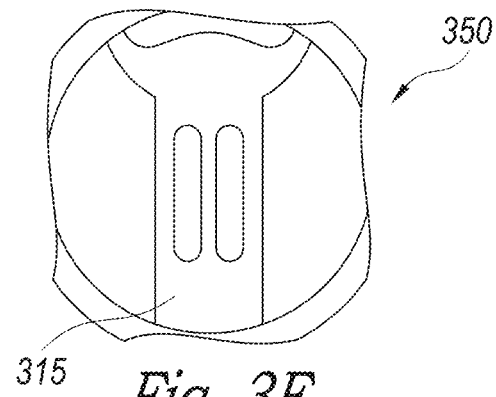
Figure 3C:
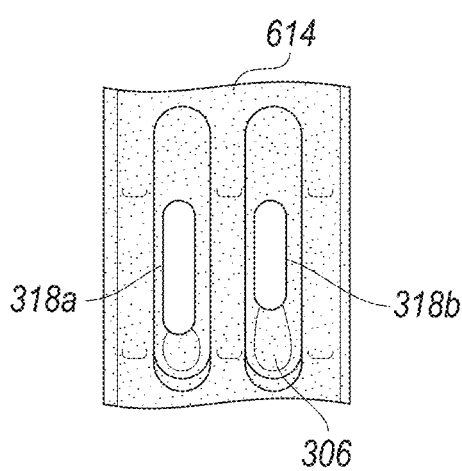
Figure 3F:
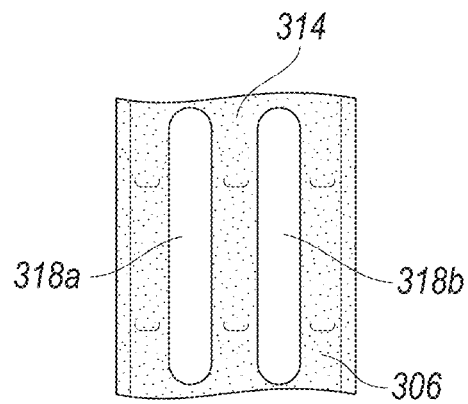

FIGS. 3A-3C illustrate a first embodiment of a spontaneous capillary flow device 300 without a controlled inlet, and FIGS. 3D-3F illustrate a second embodiment of a spontaneous capillary flow device 350 having a controlled inlet 322. As illustrated, device 300 has an open inlet 316 defined by a generally arcuate device surface 319. In contrast, device 350 has a controlled inlet 322 that confines the flowable material underneath the rail 314 as it flows from the inlet to the end of the device 350. For example, the controlled inlet 322 includes a device surface 319 that extends towards an opposite edge of the controlled inlet. A flow surface (not shown) of the controlled inlet can be spaced apart from the bottom substrate to promote fluid flow underneath the controlled inlet 322 and towards a flow surface of the rail 314. In some embodiments, the controlled inlet 322 can also contain a height gradient that can direct the flowable material towards the middle of the controlled inlet 322, thereby enabling the user to load the flowable material by placing a pipette anywhere in the loading zone. FIG. 3B is a bottom view of device 300 and FIG. 3D is a bottom view of device 350. FIGS. 3B and 3D show the flow surfaces 315 for flow devices 300 and 350, respectively. FIG. 3C illustrates the device 300 filled with hydrogel and depicts uncontrolled wetting of the culture chambers 318a and 318b. FIG. 3F illustrates the device 350 filled with hydrogel without uncontrolled wetting of the chambers 318a and 318b (e.g., cell culture zones). As illustrated, the addition of a controlled inlet 322 can reduce uncontrolled wetting of culture chambers.

Figure 4A:
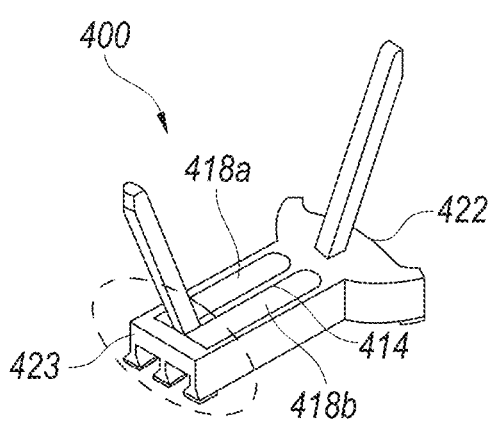
FIGS. 4A-4F illustrate flow devices with and without capillary sinks and configured in accordance with select embodiments of the present technology.
Figure 4D:
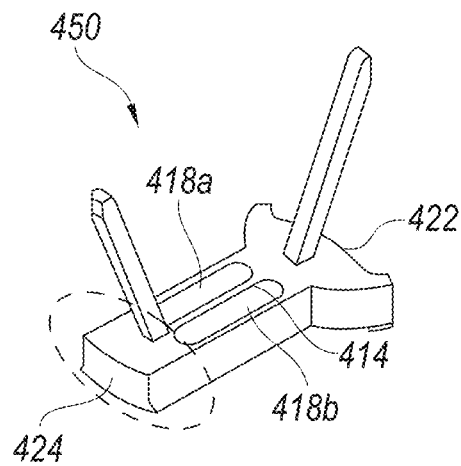
Figure 4B:
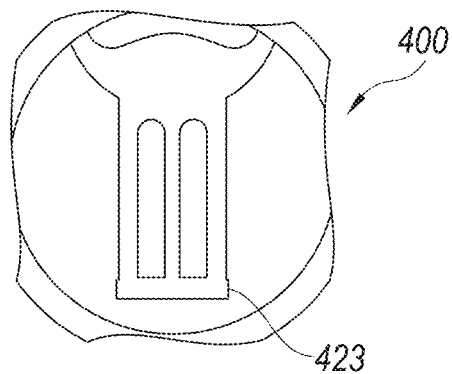
Figure 4E:
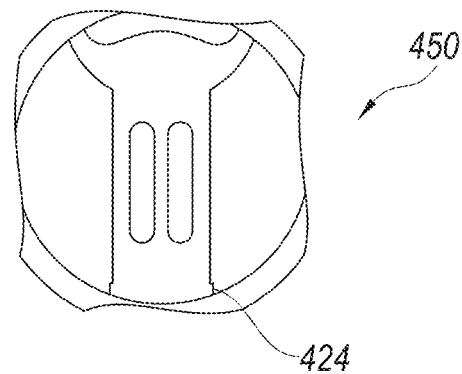
Figure 4C:
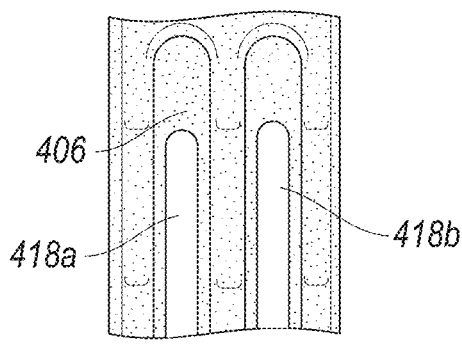
Figure 4F:
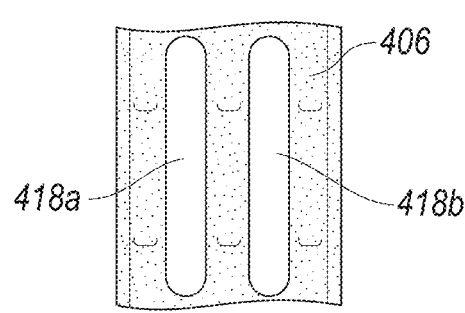

FIGS. 4A-4C illustrate a first embodiment of a spontaneous capillary flow device 400 without a capillary sink at a distal end portion of the device, and FIGS. 4D-4F illustrate a second embodiment of a spontaneous capillary flow device 450 with a capillary sink at the distal end portion of the device. As used herein, "capillary sink" refers to a region having high capillary favorability. FIGS. 4A and 4B illustrate a device 400 with a first end region having an inlet 422 and a second end portion 423 without a capillary sink. FIGS. 4D and 4E illustrate device 450 including a first end portion having an inlet 422, a second end portion 424, and a rail 414 extending between the first end portion and the second end portion 424. The rail 414 can include a flow surface (not shown) that defines a flow path for a flowable material 406. In embodiments having a capillary sink, at least a portion of the second end portion contains a region with higher capillary favorability than the inlet 422 and/or the flow surface of the rail 414 to promote flow between the first end portion and the second end portion 424. As illustrated in FIGS. 4C and 4F respectively, devices with a capillary sink at the second end portion may exhibit better flow without flooding into culture chambers 418a and 418b (e.g., cell culture zones). For example, the capillary sink can promote controlled flow because of an increased favorability of the hydrogel to wet a feature with a larger width (resulting from a lower h:w ratio, as h is kept constant from the rail to the skin), therefore, inputted hydrogel preferentially flows to the capillary sink instead of into the culture chambers.

FIGS. 5A-5F illustrate a first embodiment of a spontaneous capillary flow device 500 with a rectangular rail base portion, and a second embodiment of a spontaneous capillary flow device 550 with a trapezoidal rail base portion. As the channels are open, there is a potential for the fluid to wick vertically up along the sides of the rails, a phenomenon known as capillary rise (see, e.g., FIG. 3C). As illustrated in FIGS. 5A-5C, the rectangular configuration of device 500 can cause capillary rise, which can lead to an increased width at the base of the rail 514a and flooding into the chambers (e.g., cell culture chambers, not shown) while in the process of device filling. At the conclusion of device filing, the hydrogel can recede back towards the rail, leaving a faint residue on the surface where the gel had originally flooded into the culture chamber. To halt capillary rise of the hydrogel, the device 550 is designed to increase the pinning ability of the rail. FIG. 5C, for example, illustrates the rail 514b having a base 521. The base 521 includes a flow surface 515b, a first side 517a, and a second side 517b. The first side 517a and the second side 517b extend from the flow surface 515b and are configured to prevent capillary rise (Figure 5F). More specifically, the acuteness of the angles on the sides of the rail are increased. For example, in some embodiments, the angle defined by the flow surface 515b and the first side 517a can be less than 90 degrees. In some embodiments, the angle defined by the flow surface 515b and the first side 517a can be about 45 degrees. In other embodiments, the angle can be less than about 45 degrees. As one skilled in the art will appreciate, the angle defined between the flow surface 515b and the first side 517a can be the same or different than the angle defined by the flow surface 515b and the second side 517b. In some embodiments, the base 521 has a trapezoidal cross section. Even with the trapezoidal cross section area, the width of the hydrogel at the base of the hydrogel wall is greater than the width of the flow surface 515b because the bottom surface of the hydrogel 506 is not bound laterally (see, e.g., FIG. 5F). However, the width at the base is consistent, with the extend of flooding less than about 260 μm into the chamber, and therefore can be accounted for when designing platform dimensions.

Another source of potential flow error (e.g., chamber flooding) are Concus-Finn filaments (i.e., filaments of fluid in a wedge defined by surfaces intersecting) that may occur when rails change direction, split, or merge. The Concus-Finn filaments can be reduced and/or prevented by rounding some or all of the concave angles of the device. By removing wedge-shaped regions conducive to Concus-Finn flow, flow within the systems can more closely resemble a solid fluid front (e.g., without additional fluid filaments). As one skilled in the art will appreciate, any of the foregoing design modifications can be combined to increase flow control of the devices and systems described herein.

A number of different workflow possibilities exist for using the devices described above with respect to FIGS. 1A-5F which may be useful for different applications: (1) the device can be left in place during the whole experiment (throughout cell culture); (2) the device can be removed after hydrogel patterning, leaving behind a free-standing hydrogel wall on the bottom surface; (3) the device can be surface functionalized to enable the hydrogel to adhere preferentially to the rail such that when the device is removed, the hydrogel wall is also removed (for example, this would be useful to initially seed cells into different compartments, wait for the cells to adhere, and then remove the wall to allow cell migration after wall removal). Moreover, the flow devices and methods described herein can be used to flow a gel and then enable it to recede. This would enable full walls to be built in one area and partial coating (thinner layer of gel) to be deposited in another area. Thin layers of gel are required for the culture of certain cell types.

Flow Characteristics

The present technology utilizes spontaneous capillary flow and suspended capillary flow systems to build hydrogel partitions. More specifically, the present technology utilizes open microfluidic rail systems, in which liquid flows in a channel with no side-walls. The cross-section of the open channel thus defines a wetted perimeter ($P_w$), comprising a top flow surface (e.g., the flow surface 215 described above with respect to FIGS. 2A-2E) and a bottom flow surface (e.g., the cell culture substrate surface), and a free perimeter ($P_f$), comprising all the open interfaces.

Figures 1, 6A:
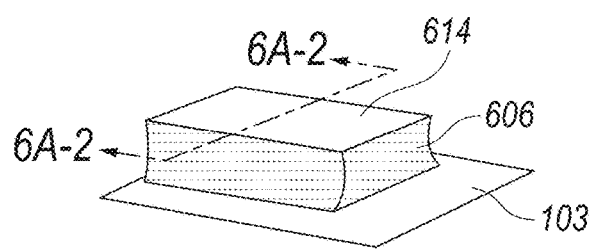
FIGS. 6A-1-6C are schematic illustrates depicting certain flow device parameters used to determine flow characteristics in accordance with select embodiments of the present technology.
Figures 2, 6A:
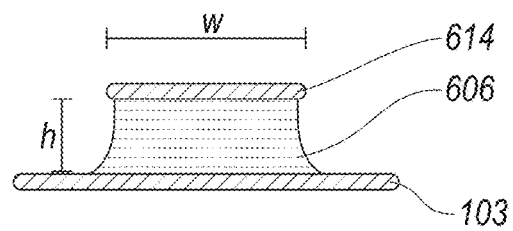

Flow within suspended capillary flow systems described herein is dependent upon the height (h) and the width (w) of the rail's flow surface. FIG. 6A-1 illustrates a flow surface 615 suspended over a cell culture substrate 103. A flowable material 306 is depicted between the flow surface 615 and the cell culture substrate 103. FIG. 6A-2 further illustrates a cross-section of the flow surface 615, flowable material 606, and cell culture substrate 103, with the height labeled (h) and the width labeled (w). The height and width of the system can control flow within the system. As such, the height and width of the system can be used to customize the open microfluidic systems described herein, in which the Laplace pressure affects the performance of a system with different aspect ratios or shapes (see, e.g., FIGS. 11A-11C). The overall conditions for spontaneous capillary flow can be defined as:

$$\frac{h}{w} < \frac{\cos \theta_1 + \cos \theta_2}{2} \quad \text{(Eq. 1)}$$

Figure 6B:
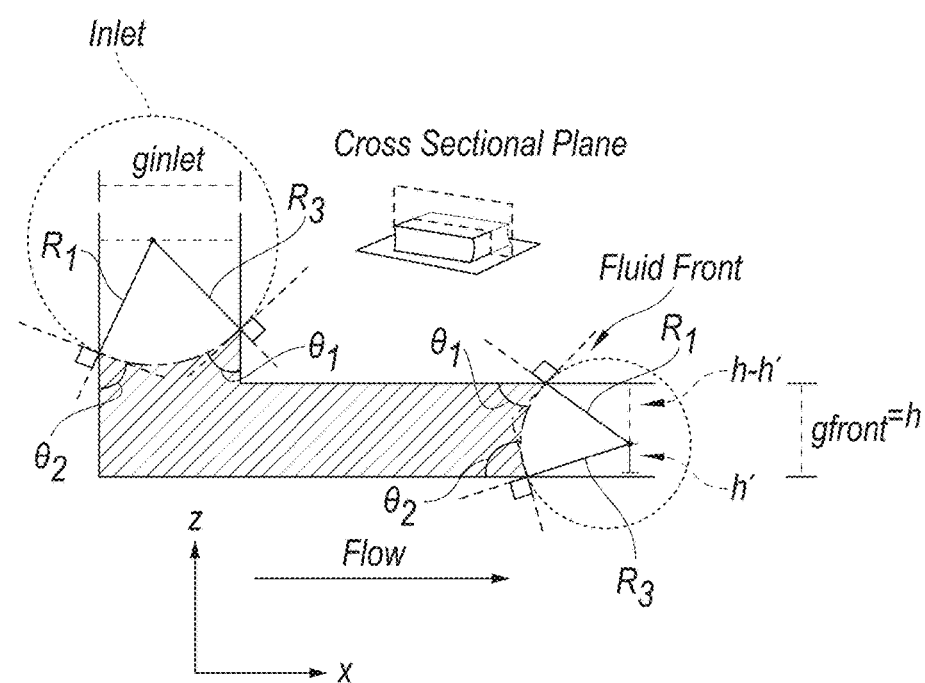
Figure 6C:
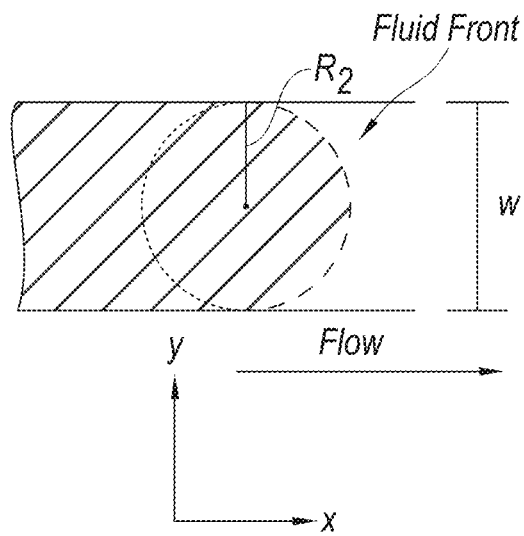

To further characterize fluid flow in the systems, a balance-of-pressure analysis can be performed between the inlet surface tension-based Laplace pressure and the Laplace pressure in the advancing fluid under the rail. FIGS. 6B and 6C illustrate certain parameters used in developing a model to characterize fluid flow. The pressure in the aqueous phase is generated by surface tension and can be evaluated using the Young-Laplace equation, where ΔP is the pressure difference across a curved air-liquid interface, γ is the interfacial tension, and $R_1$ and $R_2$ are the radii of curvature of the interface at a point on the interface in two orthogonal directions (e.g., horizontal and vertical). The Laplace pressure difference (ΔP) at every interface is zero when the interface is flat ($R_1=R_2=\infty$). When the curvature of an interface is concave due to favorable wetting (i.e., contact angle <90°), the Laplace pressure difference becomes negative. Inversely, when the curvature is convex, the Laplace pressure difference becomes positive. Laplace pressure is a well-defined phenomenon that can be controlled experimentally and used to predict conditions for flow in the systems described herein. Conditions for flow in an open channel can be derived in a general way and are known as the spontaneous capillary flow (SCF) equation (in the case of a channel that has the same contact angle on all faces) or as the generalized Cassie angle equation (for the more general case when there are any number of contact angles along the surface of the channel). The current analytical models, however, assume that the pressure at the inlet of the open channel is negligible. The models allow prediction of the theoretical ability for SCF to occur. In order to refine the conditions for flow in the systems described herein, a pressure balance analysis between the surface tension-based pressures at the inlet and at the advancing fluid front (assuming the front exists) in included.

The inlet can be a rectangular cross-section defined by the insert and the walls of the well plate. The liquid meniscus at the inlet can be concave due to the wettability of the insert and well (contact angle <90°) and the interface can take the shape of a cylinder (as the channel cross-section is long (8.6 mm) and narrow (1 mm)). The radius of curvature along the long edge of the channel inlet is thus infinitely large, while the radius of curvature $R_3$ along the smaller edge of the inlet is uniquely characterized by two different contact angles with the device insert and the well plate, respectively (see, e.g. FIG. 3B). The pressure of the fluid at the inlet is written as:

$$\Delta P_{inlet} = \gamma\left(\frac{1}{R_3}\right) \quad \text{(Eq. 2)}$$

The fluid front advancing under the rail 614 has a more complex geometry. The fluid front is described by a saddle point as the liquid is wetting the flow surface and well floor (creating a concave fluid interface in the x-z plane) and is rounded from the top view as the channel does not have any side walls (the interface is convex in the x-y plane, see, e.g., FIGS. 6B and 6C). The pressure at the fluid front is described by Equation 3, where $R_1$ is chosen to be the radius of curvature in the x-z plane, and $R_2$ is chosen as the radius of curvature in the x-y plane:

$$\Delta P_{front} = \gamma\left(\frac{1}{R_1} + \frac{1}{R_2}\right) \quad \text{(Eq. 3)}$$

For flow to occur, the Laplace pressure of the inlet should be greater than the Laplace pressure at the fluid front in order to drive the fluid towards the area of lowest pressure:

$$\gamma\left(\frac{1}{R_3}\right) > \gamma\left(\frac{1}{R_1} + \frac{1}{R_2}\right) \quad \text{(Eq. 4)}$$

Therefore, the limit of flow will occur when the two pressures are equal:

$$\gamma\left(\frac{1}{R_3}\right) = \gamma\left(\frac{1}{R_1} + \frac{1}{R_2}\right) \quad \text{(Eq. 5)}$$

Or:

$$\frac{1}{R_1} + \frac{1}{R_2} - \frac{1}{R_3} = 0 \quad \text{(Eq. 6)}$$

The radii of curvature in the system are governed by the physical aspect ratio of the channel, which includes the width (w) of the rail and the gap $g_{front}$ between the rail and the well plate ($g_{front}$=h), the gap $g_{inlet}$ between the insert and the well wall, and the contact angles of the fluid on the rail and the well plate surfaces. The radius of curvature of the fluid in the advancing filament in the x-z plane can be expressed as a function of the contact angles of the fluid on the well plate ($\theta_2$), the contact angle of the fluid on the rail ($\theta_1$), and the height of the rail (h). Using the geometric relations illustrated in FIGS. 3B and 3C, the function is:

$$R_1 = -\left(\frac{h}{\cos\theta_1 + \cos\theta_2}\right) \quad \text{(Eq. 7)}$$

To assess the curvature of radius $R_2$, the fluid is assumed to minimize the surface energy, and thus the interface takes the shape of a large semi-circle of the same radius as the half-width of the rail. Using the same reasoning utilized to determine R1 in Equation 7, R3, as a function of $g_{inlet}$, $\theta_2$, and $\theta_1$, can be derived. Substitution of $R_1$, $R_2$, and $R_3$ into Equation 7 yields:

$$\frac{1}{-\left(\frac{h}{\cos\theta_1 + \cos\theta_2}\right)} + \frac{1}{\frac{w}{2}} - \frac{1}{-\left(\frac{g_{inlet}}{\cos\theta_1 + \cos\theta_2}\right)} = 0 \quad \text{(Eq. 8)}$$

Where w is the width of the rail, h is the height of the rail, and $g_{inlet}$ is the space between the well and the device at the inlet in millimeters. Solving for h yields:

$$h = \frac{\cos\theta_1 + \cos\theta_2}{\frac{2}{w} + \frac{\cos\theta_1 + \cos\theta_2}{g_{inlet}}} \quad \text{(Eq. 9)}$$

Figure 7:
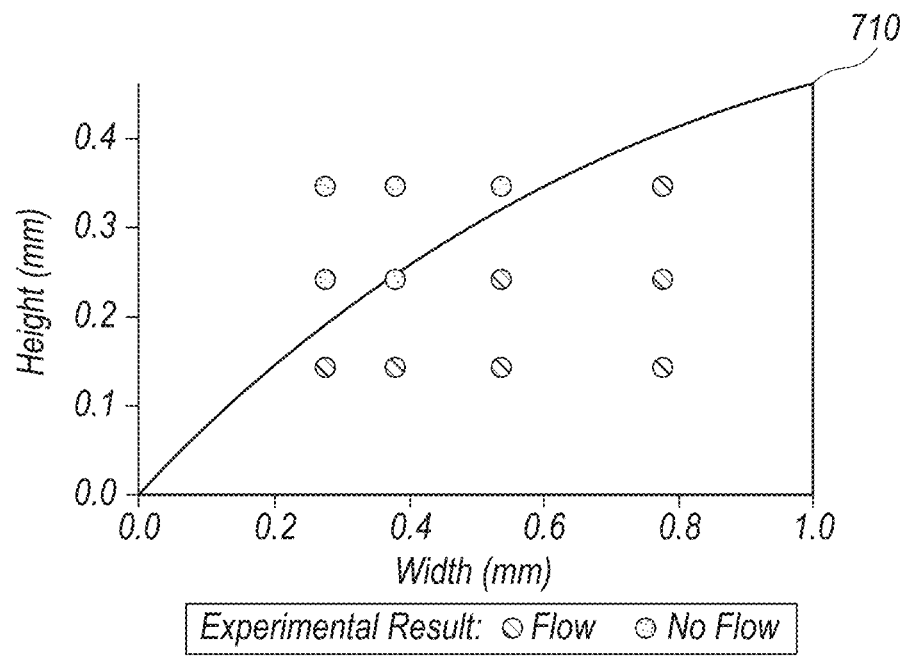
FIG. 7 is a graph illustrating device parameters suitable for flow in accordance with select embodiments of the present technology.

FIG. 7 is a graph of Equation 9 and illustrates a line 710 between the "flow" and "no flow" conditions. The area below the line 710 represents favorable flow conditions, and the area above the line 710 represents "no flow" conditions. The model was tested and validated with a range of heights and widths (experimental points in FIG. 7), in which only one experimental point showed a deviation. Moreover, the experimental data supported an expected experimental trend, in which larger widths and smaller heights promoted flow. As one skilled in the art will appreciate, this trend will likely hold true for dimensions below those explicitly discussed herein. As such, FIG. 7 and Equation 9 provide a model to predict when flow will occur in devices based on the device dimensions.

In some embodiments, the devices described herein have a height of about 0.10 to 0.40 millimeters. In some embodiments, the devices described herein can have a width of about 0.25 to about 2.25 millimeters. As one skilled in the art will appreciate, however, the devices described herein can be sized to fit any well or provide any size hydrogel wall desired. The dimensions of such customized device can be determined using Equation 1, Equation 9 and/or FIG. 7.

Fabrication of Flow Devices

The spontaneous capillary flow devices described herein can be fabricated through a variety of methods including, for example, 3D printing and injection molding. Widespread adoption of microscale cell culture systems in biomedical applications is challenging because of the need for low cost production, reproducible manufacturing, and the ability to iterate on designs. Common methods for microfluidic device fabrication, which include micro-machining, soft lithography, hot embossing, and 3D printing, are better suited for early stage prototyping than mass production. Accordingly, injection molding is the gold standard for mass manufacturing and offers high reproducibility and fast manufacturing times. However, the downside of injection molding has been the high cost (up to tens of thousands of dollars) associated with producing complex high-quality steel molds. The advent of rapid injection molding (RIM) has recently lowered the initial mold cost significantly, and with this, microscale cell culture systems are now poised for high volume use in biological and clinical applications.

The present technology provides features that facilitate the fabrication of devices described herein by RIM. Accordingly, these features are expected to enable the devices to be produced with a number of advantages over conventionally fabricated devices, including high fidelity, reproducibility, and production of large numbers of devices at a relatively low cost per device. Before discussing the specific features of the devices, a brief overview of injection molding may be helpful. Injection molding is a fabrication method in which the geometry of a part is cut as the negative space inside a separate part, called the mold, and molten polymer is forced into the mold though an opening called a gate. Once the polymer cools, the mold is separated, the part is ejected, and the mold is reused to make more parts. The ability to produce many parts from a master template (e.g., the mold) in an automated fashion makes injection molding an attractive fabrication method for high throughput production of plastic or elastomer parts. RIM is a relatively new type of injection molding that is much cheaper than class injection molding, making it far more accessible to a wide consumer-base, including, for example, academic labs. Unlike traditional fabrication methods such as micro-milling and 3D printing, RIM enables researches to make large volumes (e.g., about 500-10,000) of spontaneous capillary flow devices at a relatively low price. Because of this, RIM fills a specific niche in microfluidic technology development—the convergence of novel cell culture technologies and large-scale experimentation. However, RIM does impose relatively stringent design constraints on parts in order to keep the mold simple and the price low. For example, every face of the part must be visible from either the top or the bottom of the part. Accordingly, every vertical face of a part must be drafted, or angled slightly. Moreover, while the microfluidic devices discussed herein are capable of being manufactured by RIM, conventional microfluidics cannot because they involve closed capillaries not conducive to injection molding.

Figure 8A:
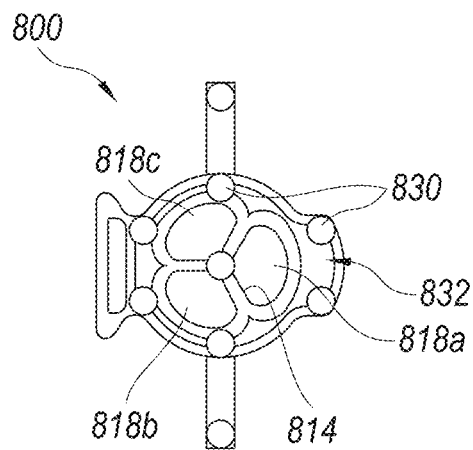
FIGS. 8A-8B are isometric illustrations of a first injection molded flow device configured in accordance with select embodiments of the present technology.
Figure 8B:
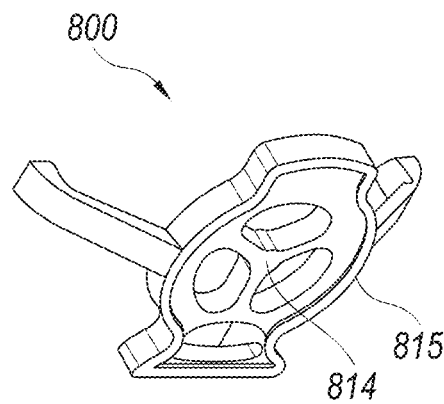

In some embodiments, the devices described herein can be fabricated with a two-sided mold. For example, FIGS. 8A and 8B illustrate the top surface and the bottom surface of a triculture device 800 having a rail 814 defining a first chamber 818a, a second chamber 818b, and a third chamber 818c. When the A and B sides of a mold come together (not shown), the void space in between them constitutes the volume that the molten plastic fills, which ultimately becomes the molded part 800 as illustrated in FIGS. 8A and 8B. Tow-sided molds offer the simplest and cheapest incarnation of RIM, although more complicated incarnations of RIM that are less stringent on part design but more expensive are possible. After the part is molded, the molten polymer is allowed to cool. This shrinking process can cause shrinking in thicker areas of the part due to a differential cooling time between thick and thin areas in the part. This shrinking can manifest as "sunken" areas in a part, where surfaces of the part that were designed to be flat come out as concave and sunken into the part. Coring out think areas of the part, or removing material from the part, can mitigate shrinkage anomalies. As illustrated in FIGS. 8A and 8B, the top surface of device 800 includes cored regions 832 to prevent and/or reduce shrinkage and deformation during the cooling process.

Figure 9A:
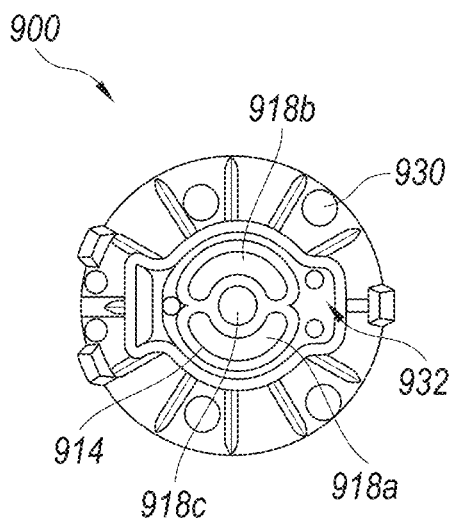
FIGS. 9A-9B are isometric illustrations of a second injection molded flow device configured in accordance with select embodiments of the present technology.
Figure 9B:
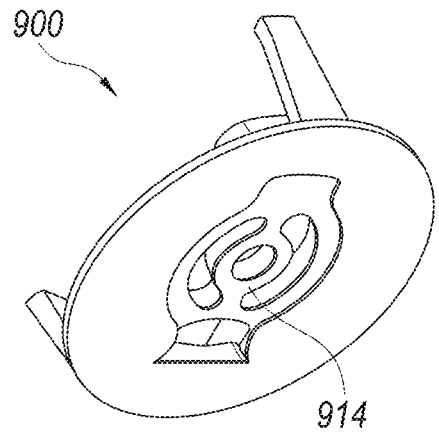

Once the part is cooled and the two sides of the mold are separated, the part must be ejected from the mold. The present technology provides a plurality of ejector pins 830 to push the part out of the mold after the molding process is complete. The ejector pins 830 are placed around the mold such that an even force is applied across the entire part during the ejection process. Moreover, in embodiments fabricated via RIM and incorporating the ejector pins 830, the devices are designed with space for these ejector pins to push against. FIGS. 9A and 9B illustrate the top surface and the bottom surface of a microculture device 900 having a rail 914 defining a first chamber 918a, a second chamber 918b, and a third chamber 918c. Device 900 also includes cored regions 932 and a plurality of ejector pins 930 to facilitate fabrication via RIM.

FIGS. 10A and 10B further illustrate a flow device 1000 designed for fabrication via injection molding. The flow device 1000 includes a rail 1014 defining a first chamber 1018a and a second chamber 1018b. The flow device 1000 includes the plurality of ejector pins 1030 and a cored region 1032 to maintain a homogenous device thickness and avoid device deformation during cooling. The device 1000 also illustrates re-positioned pressure struts 1020a-c to avoid overhang, allowing fabrication with a two-piece mold. Further, the entire device is drafted to a 1° angle to aid in device removal from the mold.

Figure 11A:
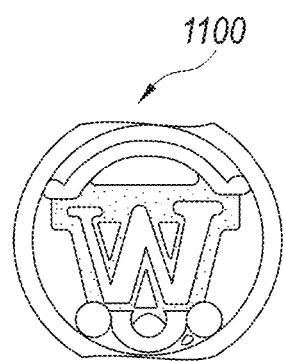
FIGS. 11A-11C illustrate various patterns the flow devices of the present disclosure can create in accordance with select embodiments of the present technology.
Figure 11B:
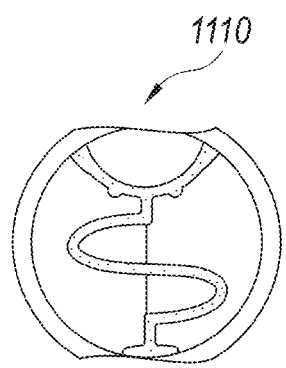
Figure 11C:
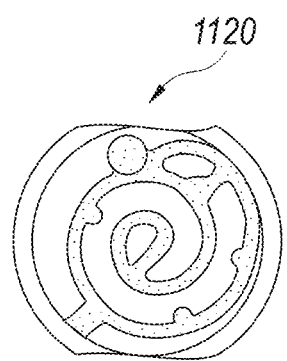

From the disclosure herein, one skilled in the art will recognize that the patterning devices described herein can be designed to create any number of potential patterns. When combined with the ability to be fabricated via low cost RIM, the potential possibilities increase. FIGS. 11A-11C illustrate three patterns the device can make. For example, FIG. 11A illustrates a pattern 1100 of a hydrogel wall in the shape of a "W", FIG. 11B illustrates a serpentine pattern 1010, and FIG. 11C illustrates a swirled pattern 1120. However, as one skilled in the art will appreciate, the present technology is not limited to the device patterns as disclosed herein.

Select Substrates for Use with Flow Devices

The flow devices described herein can be used in a number of different applications. Because the flow surface of the rail defines the flow characteristics, the second flow surface can take a number of different configurations. For example, as described above, the flow device can be used with any cell culture substrate or imaging platform. In some embodiments the substrate can be a plastic or glass surface of a well plate, petri dish, glass slide, etc.

In addition to traditional cell culture substrates, the flow devices described herein can also be used with specialized cultureware and sensitive cell types (e.g., the surface of a chemically modified well plate, chemically modified petri dish, or chemically modified glass slide). As a tunable insert, the flow devices can be incorporated into any "off the shelf" well plate, including those with pretreated and coated surfaces.

Figure 12A:
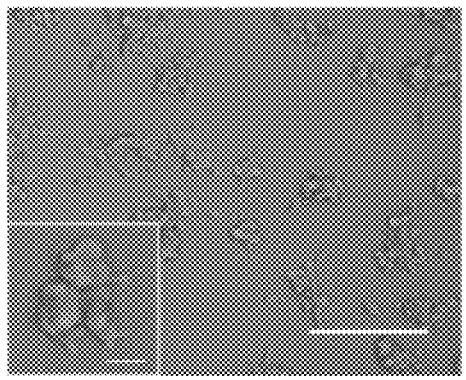
FIGS. 12A-12D are images of cells cultured in select surfaces in accordance with select embodiments of the present technology.
Figure 12B:
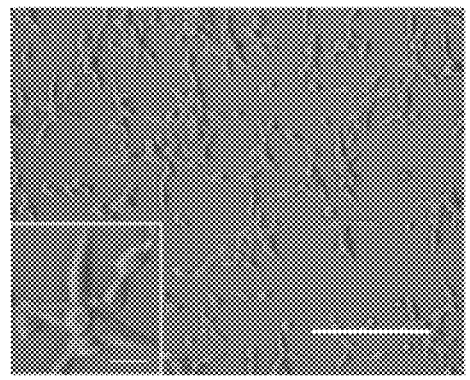
Figure 12C:
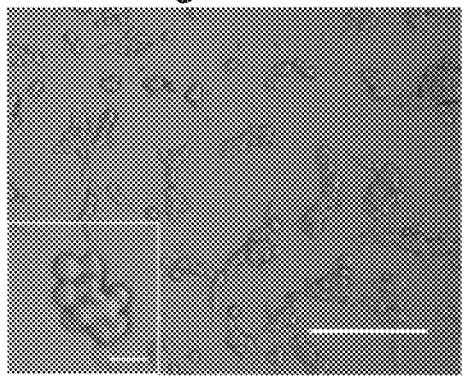
Figure 12D:
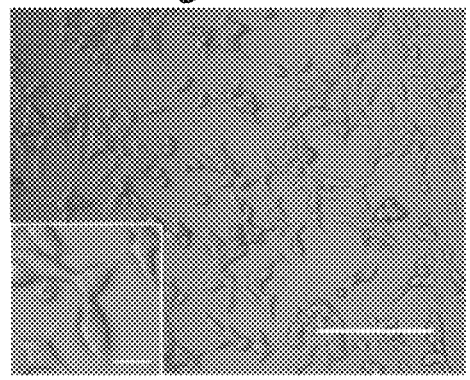

For example, as a proof of concept, the devices described herein were tested for compatibility with the human prostate cancer cell line, LNCaP, which is sensitive to culture surface chemistry and that grows better on plates with surface chemistry tuned for improved adherence. LNCap cells exhibit better adherence and spreading on a specialized substrate (e.g., PureCoat™ Carboxyl Ps (C-PS), Corning) than on traditional TCT-PS. To begin, hydrogel patterning was performed on the C-PS plates. After validating the compatibility of the hydrogel patterning on the C-PS plates, LNCaP cells were thawed and directly seeded on TCT PS and C-PS in the absence or presence of hydrogel walls patterned according to the present technology. FIG. 12A is an image of LNCap cells cultured on TCT PS without the presence of hydrogel walls. FIG. 12B is an image of LNCap cells cultured on C-PS without the presence of hydrogel walls. FIG. 12C is an image of LNCap cells cultured on TCT PS with the presence of hydrogel walls. FIG. 12D is an image of LNCap cells cultured on C-PS with the presence of hydrogel walls. As expected, morphological differences between LNCap cells cultured on TCT and C-PS were observed (e.g., FIGS. 12A and 12C versus FIGS. 12B and 12D), with LNCap cells cultured on C-PS displaying more spread out, adherent morphology (FIGS. 12B and 12D) than the LNCap cells cultured on TCT PS, which showed predominantly rounded morphologies (FIGS. 12A and 12C). The effect was independent of the presence of the hydrogel walls.

Select Embodiments of Flow Devices for Multikingdom Analysis

The present technology further provides flow devices that can be used to study multikingdom soluble factor signaling (e.g., signaling between bacteria, fungi, and human cells). Coculture of cell types from different kingdoms can be used to decipher complex physiological microenvironments (e.g., the human microbiome) and to better understand transkingdom relationships. However, key challenges of establishing multikingdom cocultures include differential media and culture conditions for each cell type, and the tendency of microbial cultures to overgrow human cultures. These challenges, along with the complexity of existing engineered multikingdom coculture platforms, have made it difficult for multikingdom coculture to expand into most microbiology and cell biology laboratories, with much of the current work accomplished within specialized engineered platforms, further illustrating the need for simple an easily-adapted systems that researchers can use to approach these complex environments.

Figures 1, 13A:
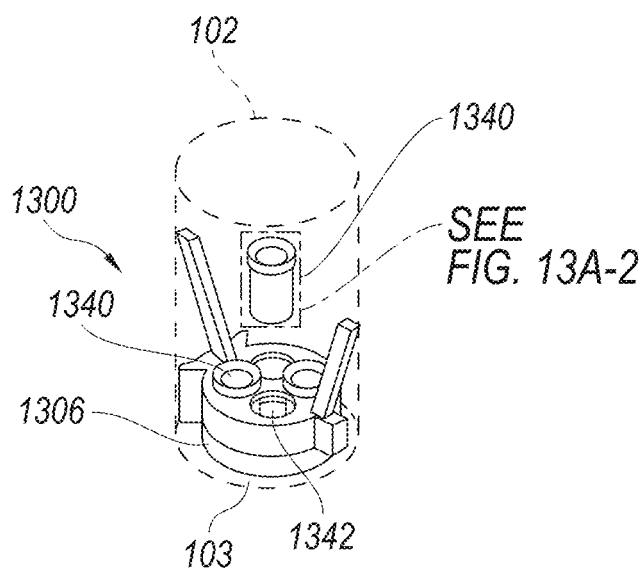
Figures 2, 13A:
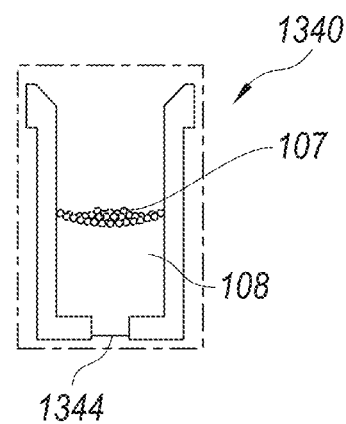

Select embodiments of the present technology thus provide modular multikingdom coculture platforms. FIG. 13A-1, for example, illustrates an embodiment of a multikingdom flow device 1300. The device 1300 includes up to four removable modular "pegs" 1340 for temporal or spatial manipulation of multiple cell types that can be inserted into matching ports 1342 on the flow device 1300. In some embodiments, the flow device 1300 can pattern a hydrogel wall to include hydrogel ports. In some embodiments, the flow device 1300 is deployed over an existing hydrogel wall patterned region 1306 on a substrate (e.g., a well surface 103). In some embodiments, hydrogel can be added to the pegs 1340 to create a plurality of hydrogel pegs sized to fit within the matching ports 1342. Modularity of the individual culture compartments (e.g., pegs 1340 and/or hydrogel pegs and the hydrogel patterned wall 1306) allows users to separately culture each kingdom in its optimized conditions before combining the compartments to initiate soluble factor signaling. As illustrated in the cross-sectional view of a peg 1340 in FIG. 12A-2, each of the pegs 1340 can include a diffusion pore 1344 that can place the interior volume of the pegs 1340 in fluid communication with the hydrogel wall patterned region 1306 on the cell culture substrate. The pegs 1340 can be filled with a culture media 108 and include cells for culturing 107.

Figure 13C:
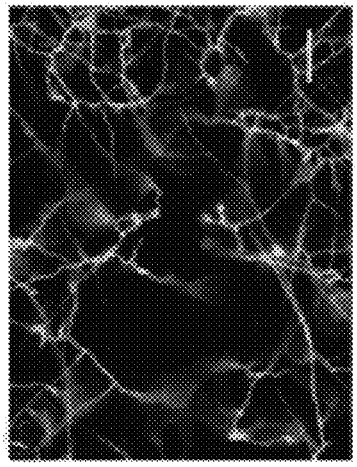
Figure 13D:
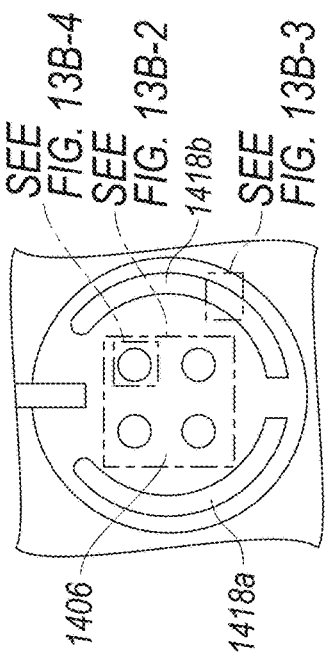
Figure 13E:
Figure 13F:
Figures 1, 13B:
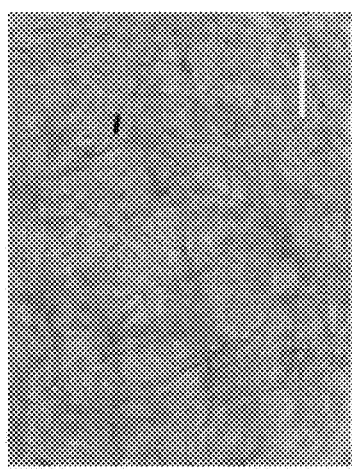
Figures 2, 13B:
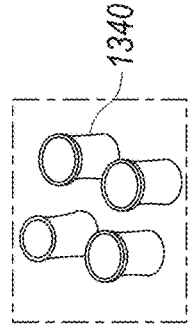
Figures 4, 13B:
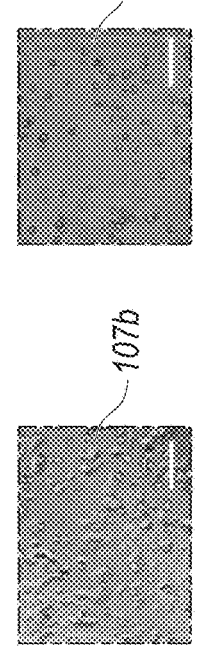
Figures 3, 13B:
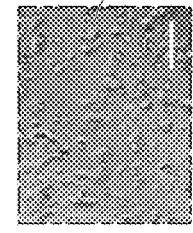

To validate the physical device workflow, a model yeast organism (*S. cerevisiae*) was combined with model adherent and non-adherent human cells (BHPrS1 and Jurkat E6.1 cells, respectively). *S. cerevisiae* was cultured atop agar-filled pegs (see, e.g., FIG. 13A-2), while the BHPrS1 and Jurkat E6.1 cells were cultured in their own media in hydrogel-defined culture chambers. After overnight incubation, the three separate cultures were combined by insertion of the *S. cerevisiae*-containing peg into the hydrogel patterned ring containing human cells (see, e.g., FIG. 13B1-4). FIG. 13B-1 illustrates a hydrogel patterned ring 1406 having a plurality of ports 1342 as well as a first cell culture chamber 1318a and a second cell culture chamber 1318b. A plurality of pegs incubated with a bacteria or fungi cell line 107b (e.g. *S. cervisiae*) can be incubated in pegs 1340 and inserted into the ports 1342, while a human cell line 107a is incubated in the first and second cell culture chambers 1318a, 1318b. FIG. 13B-3 is an image of the human cell lines from chambers 1318a, 1318b, and FIG. 13B-4 is an image of the *S. cervisiae* culture, demonstrating cell culture according to the present methods is viable.

Figure 13G:
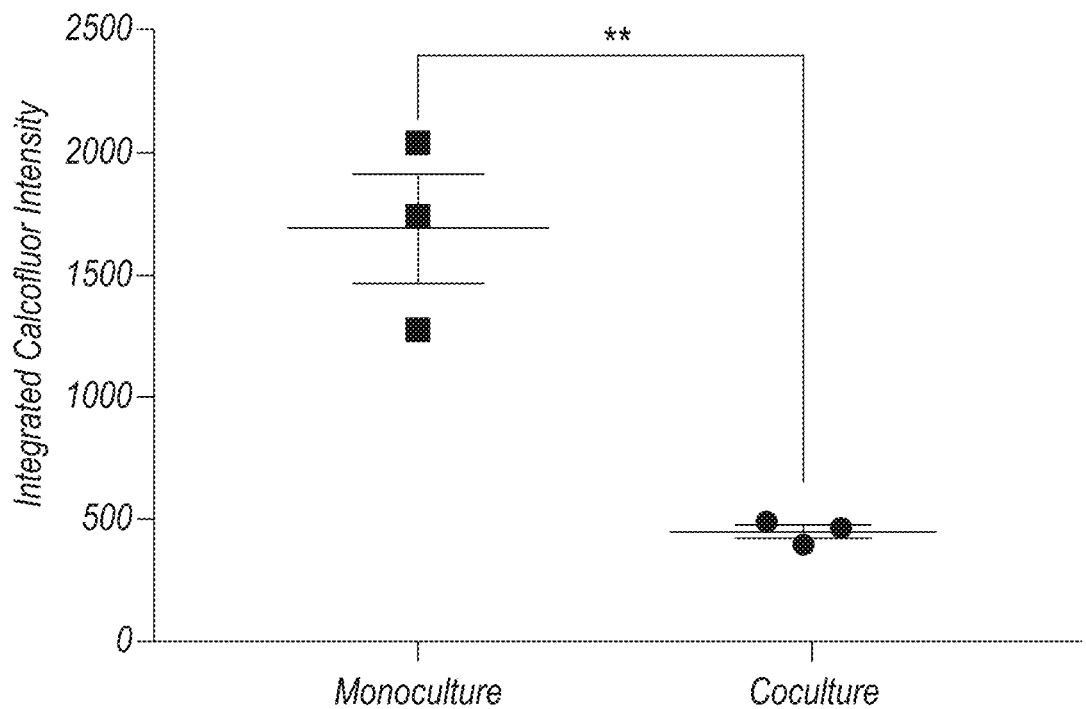

A separate multikingdom coculture system of two human pathogenic microbes, *A. fumigatus* (fungus) and *P. aeruginosa* (bacterium) was cultured to demonstrate an additional use of the hydrogel patterning platform and to characterize the ability of the platform to permit soluble factor signaling in a multikingdom coculture. Coculture of *A. fumigatus* and *P. aeruginosa* in soluble factor contact results in reduced growth of *A. fumigatus* due to secretion of inhibitory factors by *P. aeruginosa*. Therefore, *A. fumigatus* was seeded into an inner chamber of a hydrogel-patterned well plate, in which the outer chambers were filled with media. *P. aeruginosa* was seeded into LB-agarose-filled pegs and inserted into a peg-holder directly above the *A. fumigatus*. As expected, *A. fumigatus* growth was observed before addition of *P. aeruginosa*, and addition of *P. aeruginosa* decreased growth of *A. fumigatus*. FIG. 13C is a brightfield microscopy image of *A. fumigatus* monoculture on day 1. FIG. 13D is a fluorescent image of Calcofluor white stained *A. fumigatus* in a monoculture on day 4. FIG. 13E is a brightfield microscopy image of *A. fumigatus* cocultured with *P. aeruginosa* on day 1. FIG. 13F is a fluorescent image of Calcofluor white stained *A. fumigatus* cocultured with *P. aeruginosa* on day 4. FIG. 13G is a graph quantifying Calcofluor white fluorescent signal from *A. fumigatus* in mono- and coculture conveys, and illustrates the intensity decreased in the cocultured convey, illustrating the multikingdom device operated as intended. The inhibition of *A. fumigatus* growth by *P. aeruginosa* demonstrates cellular communication between two different kingdoms, supporting the use of the modular device as a platform to study soluble factor signaling in multikingdom cultures. For example, to study signaling mechanisms between human cells and microbial pathogens, human cell types such as lung endothelial or epithelial cells could be incorporated into separate culture chambers within the modular device. The modularity of the multikingdom device, in addition to the customizability of the rail-based flow systems described herein, demonstrate the potential of the multikingdom platform as a simple yet versatile tool for studying multikingdom communication.

Evaporation Control for Flow Devices

Open microfluidic systems as described herein offer the advantage of total pipet accessibility while closed systems are accessible only from strategically placed ports. However, the relatively large area of exposed liquid surface makes open microfluidic systems more susceptible to the deleterious effects of evaporation. In most cases, researchers can circumvent this problem by incubating their microculture systems in secondary containment, such as a bioassay dish. This secondary containment is often filled with a relatively large volume of 'sacrificial' water, which keeps the partial pressure of water vapor in the containment unit near equilibrium, thus mitigating evaporative water loss in the culture system. Other secondary containment strategies involve surrounding the microcultureware with wetted task wipes, in a larger container, such as light-duty wipers sold under the trademark KIMWIPES and commercially available from Kimberly Clark. A disadvantage of this approach is that the experiment can become contaminated in multi-day culture experiments. While the microscale cell culture system itself may be quite small, a large secondary containment system typically uses a lot of space in the cell culture incubator and comes with an inherent risk of liquid spilling. Finally, the need for secondary containment can be cumbersome in the hands of researchers that are not accustomed to microfluidic devices. Traditional cell culture systems are simple and more familiar to biomedical researchers. To address these disadvantages, the present technology provides a protocol to mitigate evaporative loss in the triculture device without the need for secondary containment.

Figure 14A:
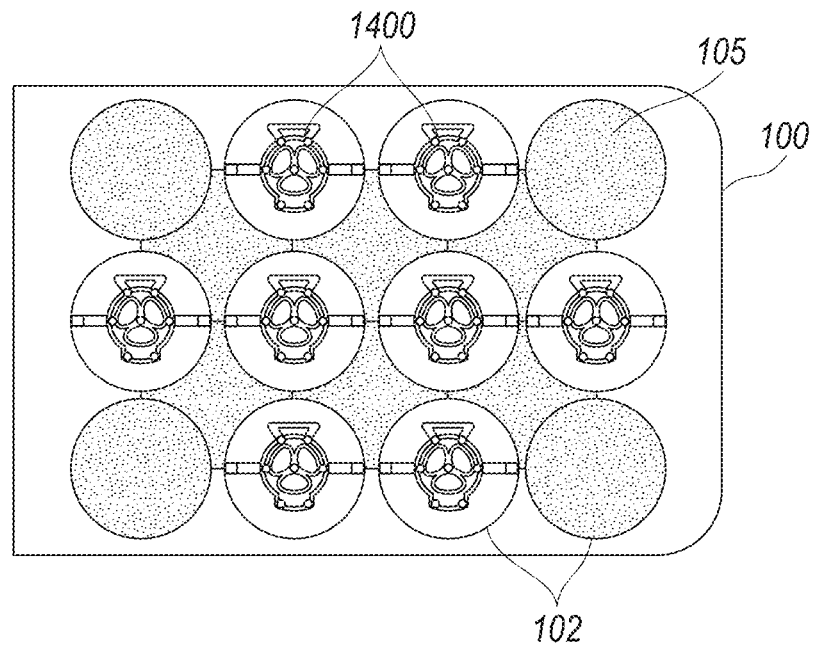
FIGS. 14A-14D illustrate techniques for mitigating evaporation and provide images validating the techniques in accordance with select embodiments of the present technology.

FIG. 14A illustrates a well plate configuration to minimize evaporative risks. More specifically, the wells 102 in the corner of the well plate 100 were filled with sacrificial water, while the remainder of the wells were filled with flow devices as 1400. To test this configuration, testis cells were cultured in the device and cell viability was measured as a qualitative metric for evaporation. Negligible evaporation was inferred in the setting of high cell viability. Cells were nearly 100% viable after 24 hours in culture when the four corner wells, as well as the spaces between the wells, were used as reservoirs for sacrificial water, as shown in FIG. 14A. This layout maximizes the number of usable wells in a well plate while keeping cell viability high. Other layouts showed dispersed pockets of dead cells throughout the well plate, likely due to evaporation in the microculture system.

Figure 14B:
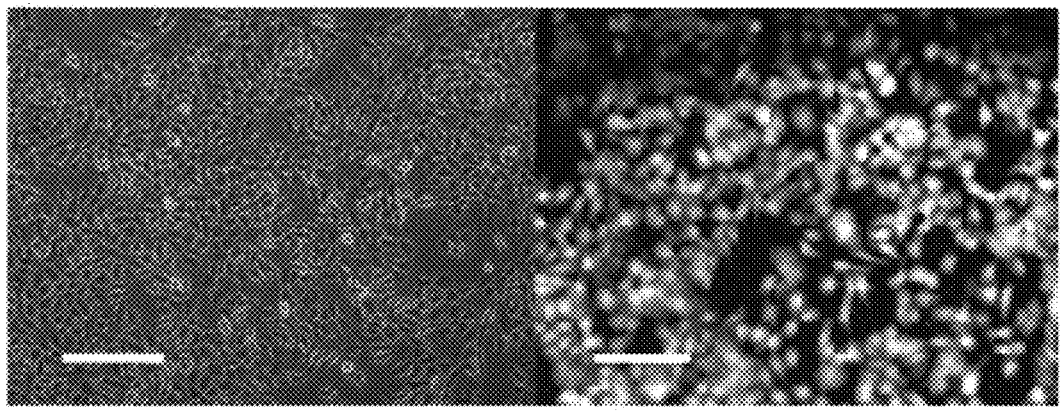
Figure 14C:
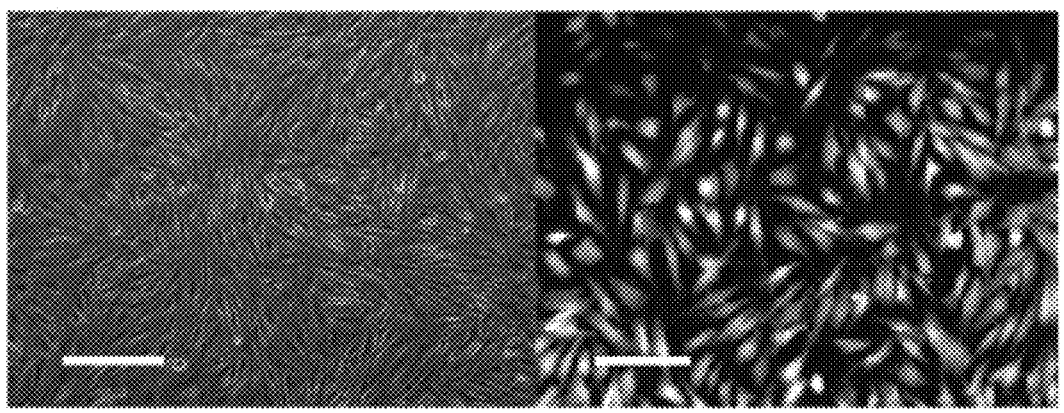
Figure 14D:
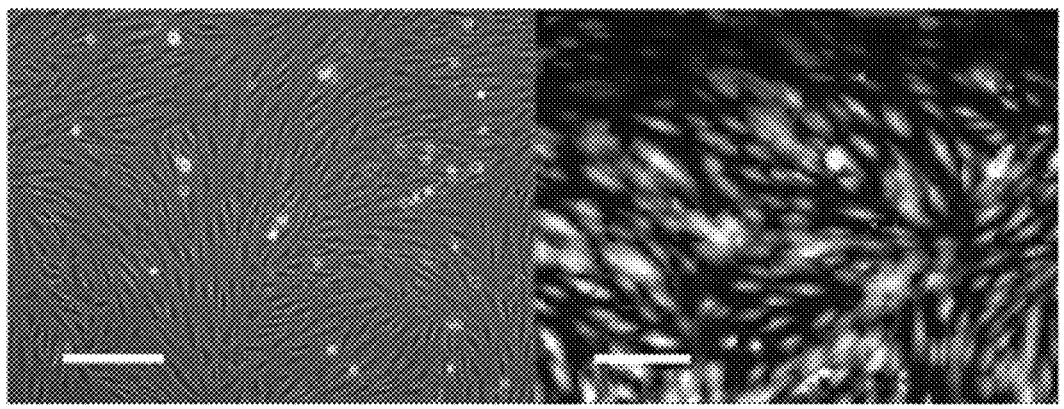

Multiple cell types were successfully cultured and showed comparable viability in the triculture device. For example, FIGS. 14B-14D illustrate MA-10 cells, BHPrS1 cells, and HLMVEC cells, respectively, cultured in the triculture device for 24 hours in the layout illustrated in FIG. 14A. Phase microscopy images illustrated expected cell morphology, and the live and dead cell staining illustrates cell viability. Without the need for secondary containment to address evaporation concerns, this device offers a simple and effective platform for co-culture experiments involving rare or difficult to culture cell types.

Select embodiments of the flow devices described herein can also include in-device evaporation control. For example, in-device evaporation control can enable co-culture experiments with rare cells, or cultures of cells that require soluble factors from supporting cells to maintain viability in vitro. To address this need, FIGS. 15A-15B illustrate a microculture device 1500 having a reservoir 1535 for holding media 108. To accommodate the reservoir 1535, the microculture device features a smaller central cell culture region 118c (~3 mm2) flanked by two larger outer culture regions 1518a, 1518b, which, in some embodiments, can hold 8 and 20 uL of media, respectively. Once the hydrogel partitions are formed, the culture regions 1518a, 1518b can include a first cell type and the culture region 1518c can include a second cell type 107b, as previously described. The reservoir 1535 can extend at least partially around a periphery of the rail 1514 defining the flow path of the hydrogel walls 1506. In some embodiments, the reservoir can be defined by a barrier 1536 on a first side of the reservoir 1535 adjacent the rail 1514, and a wall 1537 on a second side of the reservoir 1535 spaced apart from the rails 1535. In some embodiments, the barrier 1536 can divide the rail 1514 and the reservoir 1535 and include a pinning ridge that pins the media and prevents media spillage into the cell culture chambers 1518a-c defined by the rails 1514.

The small volumes of media associated with coculture device 1500 necessitate a unique evaporation control strategy. FIGS. 15A and 15B show how the outer region of the device 1500 when seated into a well 102 acts as a media reservoir. When evaporation occurs from the cell culture regions 1518a-c, media 108 is immediately replenished from the media reservoir 1535. When the device 1500 is placed flush in the bottom of the well 102, there remains enough space between the base of the device 1500 and the bottom of the well 102 for water to exchange between the culture regions 1518a-c and the media reservoir 1535. The 'contact area,' or area where the device 1500 is in contact with the bottom of the well 102 (e.g., well base 103) was designed to be as large as possible to limit the diffusion of soluble factors from the culture regions 118a-c to the media reservoir 1535. Hydrogel precursor solution floods under the contact area when it is loaded into the device 1500, further mitigating diffusive loss of soluble factors to the media reservoir; however, the relatively high viscosity of most hydrogels preclude them from completely filling this space. The diffusion of a 10 kda fluorophore, which was used as a model 'soluble factor,' is limited to about 2.4% after a 24-hour incubation. To validate the mitigation of evaporative water loss, cell viability was examined and little to no cell death was observed in any part of the device, irrespective of the number of devices in the well plate or the position of a device in the well plate. Using a single well of a well plate offers the harshest condition with respect to evaporative water loss. The ability to culture small numbers of cells in a well plate compatible and pipet accessible format has the potential to simplify a wide range of difficult coculture conditions.

High Resolution Microscopy in a Coculture System

High resolution imaging is an important readout for biomedical researchers, as the intracellular location of the substance of interest (e.g., protein, mRNA) has important implications for function. Single molecule fluorescent in situ hybridization (smFISH) detects a specific mRNA transcript with multiple short oligonucleotide probes. It is particularly powerful for understanding the spatial patterns of gene expression at the level of the individual cell. This information is important for understanding the regulation of transcripts in many biological systems. The present technology facilitates high resolution microscopy of coculture systems by enabling coculture of separated populations of cells on the same plane.

Additionally, the adaptability of the devices described herein can further enhance high resolution imaging. For example, if the cells are cultured on a standard 12 well plate, microscopic imaging resolution is limited by the thickness of the well plate floor. However, imaging resolution can be much higher if cells are cultured on a thinner surface (e.g., a glass cover slip). Thus, the present technology enables cells to be cultured on a variety of thin substrates that facilitate high resolution imaging. FIGS. 16A-16D illustrate a workflow in accordance with select embodiments of the present technology. FIG. 16A, for example, illustrates a flow device 1600 having three cell culture chambers 1618a-c on a glass cover slip 1640. Once the device is on the cover slip 1640, the hydrogel can be loaded into the inlet and flow between the device 1600 and the cover slip 1640 to create the hydrogel partitions. In some embodiments, the glass coverslip can be placed in a well of a well plate before hydrogel patterning. Once the hydrogel walls are formed, cells can be cultured in the individual cell culture chambers 1618a-c. After culturing, the cells can be immunostained to prepare for imaging. As illustrated in FIG. 16B, the media can be aspirated from the cell culture chambers to expose the stained cells. As illustrated in FIG. 16C, the device 1600 can be removed from the cover slip, leaving the stained cells 107a-c behind. As illustrated in FIG. 16D, the device 1600 can then be inverted and placed on a glass slide 1642 for imaging of the stained cells 107a-c.

FIGS. 17A-17D are images of stained cells using the workflow described above with respect to FIGS. 16A-16D. FIG. 17A is an N-SIM Z-stack (total of 26 planes) image of smFISH for Star, FIG. 17B is an image of Cyp11a1 sp/mRNA from MA-10 cells, FIG. 17C is an image of DAPI stained nuclei, and FIG. 17D is an image overlaying the images of FIGS. 17A-17C. These images show no visual occlusion or distortion of immunostained cells by the hydrogel residue, supporting the compatibility of the microscale devices with high resolution imaging.

3D Printing using Select Embodiments of Flow Devices

The present technology also provides systems, devices, and methods for three-dimensional (3D) printing. The development of new three-dimensional fabrication methods often starts with the advent of a new two-dimensional (2D) layer patterning method. The main 3D printing methods today are based on layer patterning systems which work on physical principles such as extrusion of filaments through a nozzle, selective light-induced cross-linking of photo-responsive polymers, and sintering of powders using lasers.

Three-dimensional bioprinting has become a technique of interest for use in tissue engineering and biological studies. In 3D bioprinting, biological materials such as collagen and other biological hydrogels, growth factors, and cells are used to form 3D environments or structures similar to those in living organisms. Current 3D printing methods for biological materials include, microextrusion, laser-assisted, and digital light processing (DLP) bioprinting. Extrusion-based and light-based methods have advanced abilities to create biological structures for tissue engineering and biological applications. However, photoactive agents in light-based methods and shear stress in nozzle-based methods have been found to cause varying degrees of damage to certain cell types. Accordingly, a 3D patterning method that does not rely on photoinitiators nor external pressure could alleviate some of the stresses experienced by cells and open up bioprinting to cell types that are difficult to culture with current bioprinting methods.

The present technology provides a 2D patterning method that utilizes physical principles that are not found in existing 3D printing technologies and that allows layer-by-layer building of 3D structures. In some embodiments, the present technology includes a layer-by-layer patterning method that utilizes surface tension forces and open microfluidics (e.g., rail based open microfluidics described in detail herein) to subsequently pattern layers on top of each other, producing 3D hydrogel structures. Capillary pinning can enable a pre-gel solution to remain in a defined pattern set by a patterning device (e.g., the rail), which sits a distance above a previously patterned gel layer. The patterning device and the previously patterned gel layer comprise the ceiling and floor of the open microfluidic channel, through which spontaneous capillary flow of the pre-gel solution occurs. Each subsequent layer can use a unique rail with either the same pattern or a different pattern as the layer before. The substrate on which the gel structure is erected (e.g., the floor of a well plate) and the underside of a patterning device (e.g., the rail) sit substantially parallel to each other with a gap for the gel to flow through. Pre-gel solution is pipetted into the gap and flows by SCF, the material is then gelled (typically with a temperature change), and the patterning device is removed and replaced with a new patterning device for the next layer.

Figure 18B:
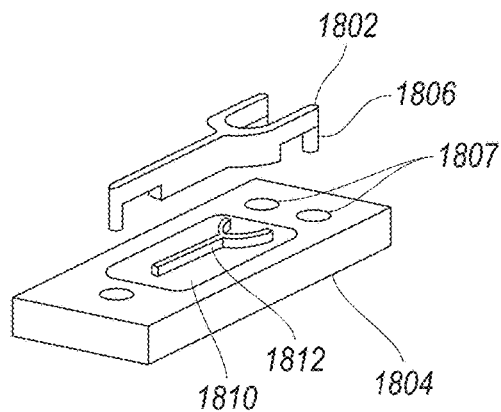

FIGS. 18A and 18B illustrate an embodiment of a flow device 1800 for use with the 3D printing techniques described herein. More specifically, FIG. 18A illustrates a device 1800 having a rail 1802 releasably secured to a base 1804 by a plurality of supports 1806 engaging a plurality of ports 1807. The rail 1802 can provide a flow surface for patterning the flow of a hydrogel, as described previously. The illustrated embodiment shows a first gel layer 1810 in the base (e.g., using a different rail with a different flow pattern), and a second gel layer 1812 being patterned by the rail 1802. The first gel layer 1810 can be a base gel layer that provides a foundation to build a specific design on, or can include a specific pattern itself. FIG. 18A further illustrates a pipette 104 delivering the hydrogel to an inlet region of the rail 1802. FIG. 18A-2 further illustrates a cross section of the patterning device 1800, and illustrates the rail 1802 suspended above the base 1804. The first gel layer 1810 sits in the base 1804, and the second gel layer 1812 is flowed over the first gel layer 1810 based on the patterning of the rail 1802. Once the hydrogel that will comprise the second gel layer 1812 has formed, the rail 1802 can be removed from the base, as illustrated in FIG. 18B. Once removed, the patterned second gel layer 1812 remains on the first gel layer 1810 in the base 1804. A second rail (not shown) with the same or a different rail pattern can then be releasably secured to the base by placing supports 1806 into ports 1807 to continue the layer-by-layer fabrication process.

FIGS. 19A-19F illustrate an embodiment of a layer-by-layer fabrication technique using a flow device 1900 in accordance with select embodiments of the present technology. Unlike the flow device 1800 of FIGS. 18A and 18B, the flow device 1900 is designed to sit flush to the floor of a well plate 102, and includes pressure struts 1906 for stabilizing the device 1900 in the well plate 102. The height of the ring 1917 around the outer portion of the device 1900 can determine the distance between the bottom of the well plate 102 and the flow surface 1915 of the rail 1914. As described above, a base portion of the rail 1914 defining the flow surface 1915 can be designed to pin the hydrogel to promote defined flow (e.g., the base portion can have a substantially trapezoidal cross-section).

Figures 19A, 19B, 19C:
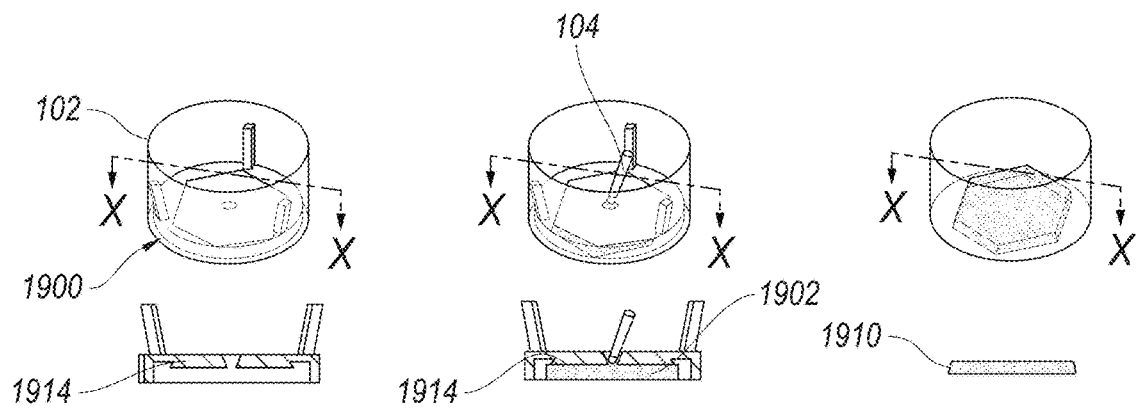
FIGS. 19A-19F illustrate a workflow for layer-by-layer fabrication of a three-dimensional structure in accordance with select embodiments of the present technology.
Figures 19D, 19E, 19F:
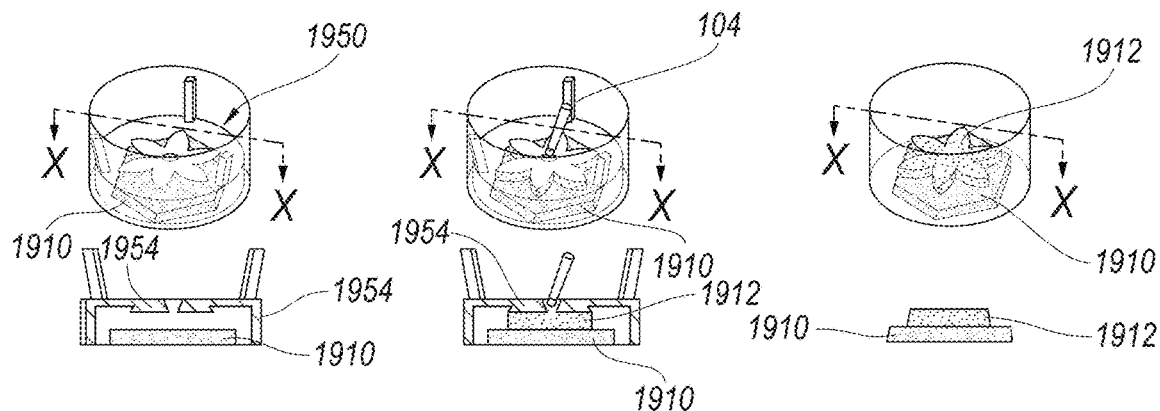

When pre-gel solution is loaded into a patterning device, it fills the 'channel,' and remains suspended between the patterning device and the underlying substrate until a polymerization trigger is introduced. In some embodiments, temperature change can be used for polymerization, although the ability to polymerize a layer after it has been patterned makes it possible to build multi layered structures of any hydrogel whose precursor solution can meet the condition for SCF. After a single layer of pre-gel solution is patterned and solidified to form gel layer 1910 using device 1900 having rail 1914 (FIGS. 19A and 19B), the patterning device 1900 is removed (FIG. 19C), and a new patterning device 1950 having a second rail 1954 is placed over the gel layer 1910 to define a new area for the next layer of gel 1912 (FIG. 19D). The patterning process is repeated for each additional layer (FIGS. 19E and 19F). Using this method, an entire layer can be added in one pipetting step, as opposed to alternative nozzle-based 3D patterning methods which require multiple passes of material deposition for a single layer.

The layer-by-layer fabrication method can be used to create a variety of structures, ranging from simple structures having a few layers to more complex three-dimensional structures having many layers (e.g., FIG. 21). For example, in some embodiments, the layer-by-layer fabrication methods are used to create structures having 10 or fewer layers. In some embodiments, however, the layer-by-layer fabrication methods can be used to create structures having more than 10 layers (e.g., 15 layers, 20 layers, 25 layers, 30 layers, 35 layers, etc.).

A design challenge for patterning three-dimensional hydrogel structures is building unsupported features (e.g., features that cantilever into air rather than building on base material underneath). Many additive manufacturing systems utilize a sacrificial material as a support, which is removed in a post-processing step either physically or chemically. In such methods, the structural integrity of the desired product must be maintained after the supports are removed, which restricts the types of materials that can be used. The present technology provides techniques for creating overhanging, unsupported structures without the use of sacrificial material by incrementally offsetting the patterning device from the edge of the previous layer such that each layer extends past the limits of the previous layer. To exemplify this concept, the schematic in FIGS. 20A-20C illustrate a rail design without an overhang (FIG. 20A) and with an overhang (FIGS. 20B and 20C). For example, in FIG. 20A, the edge 2021a of the patterning device 2000a is roughly in line with the edge of the first gel layer 2010. However, in FIG. 20B, the edge 2021b of the patterning device 2000b overhangs the edge of the first gel layer 2010 by an overhang distance marked as "s."

The length of overhang achievable was improved by the addition of a downward curvature to the edge 2021 of the patterning device 2000c to allow for favorable flow over the edge of the previous gel layer 2010 (FIG. 20C). Without the added curvature, the bottom of the fluid front pins to the edge of the previous layer as expected, but the top of the advancing pre-gel solution does not continue along the patterning device (FIG. 20B). The curvature decreases the relative ratio of the air-liquid interface to the patterning device-liquid interface; minimizing this ratio is favorable for SCF. Thus, the agarose fluid front continues along the surface of the patterning device, increasing the overhang capacity. This can result, for example, with a second gel layer 2012 extending over a first gel layer 2010 (FIG. 20C).

In order to achieve spontaneous capillary flow for all layers of an overhanging structure, the geometry of curvature can be adjusted for each layer. If each layer had the same curvature, then the maximum distance (air gap) between the two layers would become great enough that spontaneous capillary flow could be inhibited. However, by applying a calculation to change the curvature dimensions of the current layer based upon the dimensions of the previous layer, the distance between layers can be minimized, allowing for SCF. The calculation can be made as follows: for a first overhanging layer (e.g., layer 2), the radius of curvature can be set to 1 mm. Every subsequent layer's radius of curvature can be increased by 0.5 mm, i.e., layer 3 is 1.5 mm, layer 4 is 2 mm, etc. Take any layer, n, where n>1, and the radius of curvature, $r_n$ is then given by Equation (10):

$$r_n = 0.5n \quad \text{Eq. (10)}$$

As noted, layer 1 has no radius of curvature, as it is not an overhanging layer. The curvature of layer n can be designed such that the curvature begins at half the distance of the x component of the previous layer, $x_{n-1}$, which is illustrated in FIG. 21A. The x component of the curvature for layer n, x–n, is then given by taking one half of the x component of the previous layer, and adding this to the maximum overhang, 1, described in Equation (11):

$$x_n = \frac{x_{n-1}}{2} + s \quad \text{Eq. (11)}$$

Using the calculated x component and the radius of curvature for layer n, the y component of the curvature can then be derived. FIG. 21B is a geometric schematic illustrating how to calculate these layers. To calculate the angle, θ, which represents the arc angle of the circle that encompasses the curvature, the geometric relation of the radius of curvature, $r_n$, to the x component of the curvature was used, and described in Equation (12), where θ is in degrees.

$$\theta = \sin^{-1} \frac{x_n}{r_n} \quad \text{Eq. (12)}$$

Using this angle and the fact that the red dotted triangle is an isosceles triangle, the value of angle γ could be calculated using Equation (13), where γ and θ are in degrees.

$$\gamma = \frac{180 - \theta}{2} \quad \text{Eq. (13)}$$

Then, the value of $y_n$ can be calculated using Equation (14):

$$y_n = \frac{x_n}{\tan \gamma} \quad \text{Eq. (14)}$$

The layer-by-layer fabrication methods described herein can be used to produce complex shapes. FIG. 22 illustrates an agarose cylinder 2200 with hollow winding tubes in the shape of a double helix. The helix consists of 30 layers, each 500 μm thick, and has a total rotation of 270 degrees. Other 3D fabrication methods have utilized a sacrificial material to create channels through a three-dimensional hydrogel structure or have employed a casting method to create fluid channels. Furthermore, laser photoablation can be used to create microchannels through hydrogels with greater resolution, and multiphoton lithography can be used to create microchannels through cell-laden collagen structures without the potential cellular damage from photoablation techniques. The layer-by-layer fabrication method described herein, however, uses a plurality of unique rails (e.g., 2201a, 2201b, 2201c, etc.). The helix geometry also demonstrates the broader capacity to create gels with complex three-dimensional tubing and void spaces, thereby opening up the possibility of creating three-dimensional fluidic channels spanning multiple planes through a hydrogel structure without reliance on a sacrificial material or post-fabrication step.

In some embodiments, the systems and methods described herein are compatible with unmodified (e.g., native) biological hydrogels, or other nonbiological materials with fluid properties that are compatible with spontaneous capillary flow. For example, through the open-microfluidic layer-by-layer fabrication method to be described in detail above with respect to FIGS. 19A-19F, the present technology provides the capability to build agarose and collagen structures featuring asymmetric designs, multiple components, overhanging features, and human cell laden regions.

The present technology can also provide a method for recapitulating cellular environments. Recapitulating cellular environments requires spatial organization of cells and biological hydrogels in three dimensions because in vivo tissue structures are heterogeneous in composition. The open microfluidic layered patterning methods described herein provide an interesting new approach to building multi-material or multicomponent structures. For example, different materials can be introduced at every layer to create a structure with differential material properties in the Z-direction. For example, an agarose structure can be erected beginning with a concentration of 2% wt/v and decreasing 0.25% wt/v every five layers to a final concentration of 0.75% wt/v. The resulting structure thus has a stepwise concentration gradient in the Z-direction. In some embodiments, the agarose concentrations can fall within the range of relevant concentrations used for transport models of biological systems such as the brain extracellular space. As such, the layered patterning method has the potential to be extended to, for example, brain extracellular matrix modeling applications. As one skilled in the art will appreciate, the described agarose structure is provided to illustrate the capabilities of the present technology, but in no way limits the present technology.

Furthermore, the present technology provides the ability to pattern multiple materials within the same layer to enable creation of a structure with spatial organization in all three dimensions. In the present technology, a simple flow-guiding feature can be added to the patterning device to direct and segregate the flow of different materials within each layer. Many materials do not have the mechanical properties necessary to create free-standing 3D structures without the use of a second support material, presenting a challenge for many 3D bioprinting applications. To overcome this challenge, the present technology provides the ability to pattern a single layer with multiple materials. For example, a single layer can be patterned with multiple materials to create an agarose 'support' structure for unmodified type I collagen (7.5 mg/mL). Type I collagen was chosen because it is abundant in biological systems and often used in 3D bioprinting. Some commercially available 3D bioprinters are capable of printing type I collagen that has been modified to support free-standing structures (such as Bio X and Allevi printers). Additionally, protocols have been developed for 3D printing type I collagen at concentrations above and below the commercially available threshold. The present technology thus provides an alternative method for patterning layers of commercially available concentrations of unmodified collagen. An agarose border can be patterned on each layer, which can subsequently be filled with cell-free collagen. Cell-laden collagen can then be patterned over the newly established layer of collagen. Open microfluidic functionality can also be added to the top of the patterning device, where the flow is also driven by capillary action. This capability can be utilized as another method by which multiple materials can be deposited in a single layer.

Accordingly, the present technology provides a rail-based layer patterning of hydrogels. Complex structures, including unsupported overhanging features, objects comprising multiple materials and components, asymmetric designs, and cell-based architecture. Additionally, in some embodiments, the agarose and collagen do not need modified with agents to increase their structural dependability, and passive forces can be leveraged to enable the hydrogels to flow into designated patterns. Hydrogels used in current 3D bioprinting systems are often mixed with highly-reactive chemicals to initiate polymerization or crosslinking through pH changes or UV light. Free radicals are generated when chemical photoinitiators present in the hydrogels are exposed to light, which can cause oxidative damage to any embedded cells, affecting their physiology and viability. Additionally, in microextrusion, the most common form of bioprinting, the hydrogel and cell mixture is jetted through a nozzle that exposes the cells to shear stress, which can affect the physiology of the cells and limit the cell types available for use in an extrusion-based bioprinter. Furthermore, increasing nozzle size or adjusting the feed rate can enable the use of more viscous gels, but compromises the level of detail achievable in the printed structure. The present technology provides techniques that use fundamentally different principles—surface tension forces and open microfluidics—to pattern hydrogel structures.

Because the present technology provides a capacity to control the location of different gel materials within and between layers, the present technology can be used to create complex structures, such as a 3D organoid model, by directing the patterning of cell types and culture materials in 3D space. Further, building open microfluidics directly into the patterning device integrates existing microfluidic principles for guiding fluid flow with the layered patterning method.

Surface Patterning

Figure 23A:
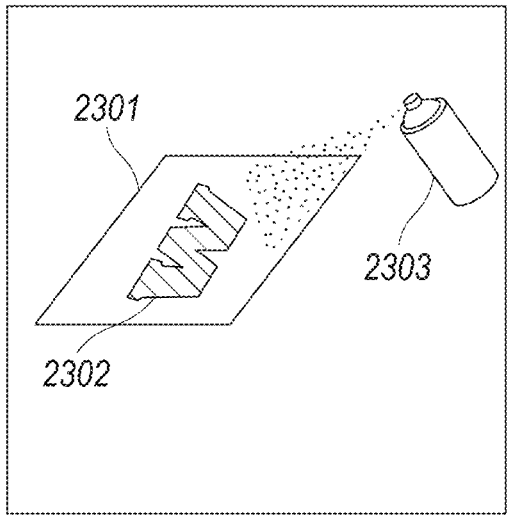
FIGS. 23A-23D illustrate a workflow for creating a three-dimensional structure using surface patterning in accordance with select embodiments of the present technology.
Figure 23B:
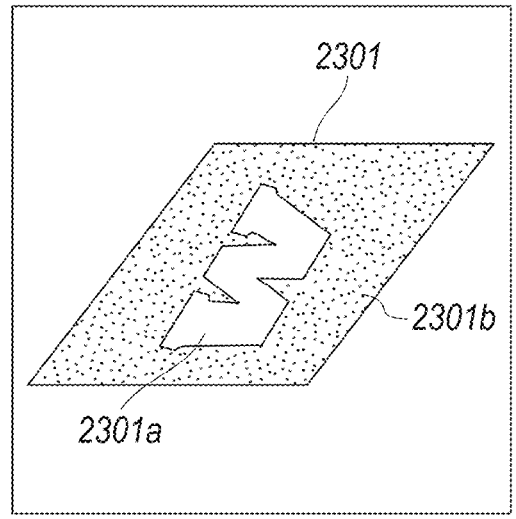
Figure 23C:
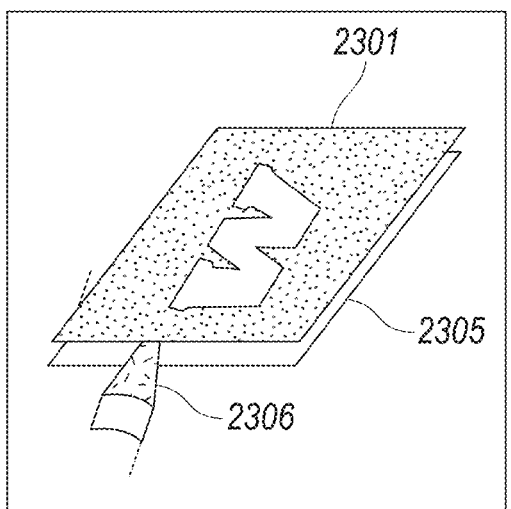
Figure 23D:
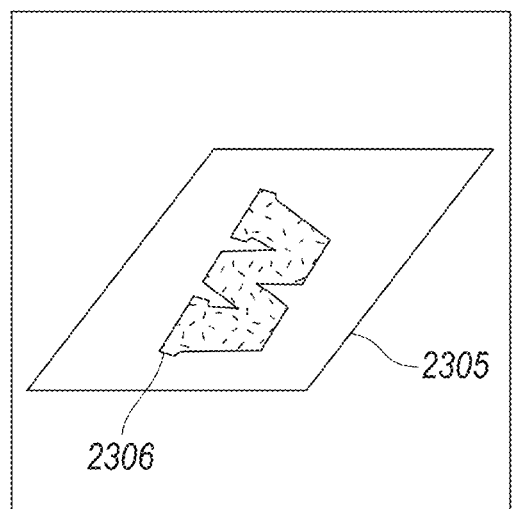

Select embodiments of the present technology further provides a workflow for creating three-dimensional structures using open microfluidics and surface patterning. FIGS. 23A-23D, for example, illustrate one embodiment of such workflow. In FIG. 23A, a mask 2302 is placed on a substrate 2301. While FIG. 23A illustrates the mask 2302 as a "W", one skilled in the art will recognize that the mask can take any shape. A hydrophobic spray 2303 can then be applied to the substrate 2301 such that it coats the entire substrate except for the portion blocked by the mask 2302. In FIG. 23B, the mask 2302 has been removed, illustrating a first portion 2301a of the substrate that remains untreated, and a second portion 2301b of the substrate that is coated in the hydrophobic spray. In FIG. 23C, the patterned substrate 2301 can be flipped upside down and positioned above a blank substrate 2305 (e.g., a hydrophilic substrate). A flowable material 2306 (e.g., hydrogel) can be injected between the patterned substrate 2301 and the blank substrate 2305. The flowable material 2306 will flow between the patterned substrate 2301 and the blank substrate 2306 guided by the first portion 2301a of the patterned substrate 2301 that remains hydrophilic. Once the flowable material is polymerized, the patterned substrate can be removed, and a patterned hydrogel remains on the blank substrate 2305, as illustrated in FIG. 23D. The process can then be repeated to build successive layers.

In some embodiments, the workflow described with respect to FIGS. 23A-23D can be automated to provide an automated 3D printer that adds to the scope of technologies available for 3D bioprinting. In some embodiments, use of surface patterning can achieve higher resolution. In some embodiments, the processing time can be improved in a future embodiment that provides tighter local temperature control, affecting faster gelling.

Select Embodiments of Cell Migration Flow Devices

Figure 24A:
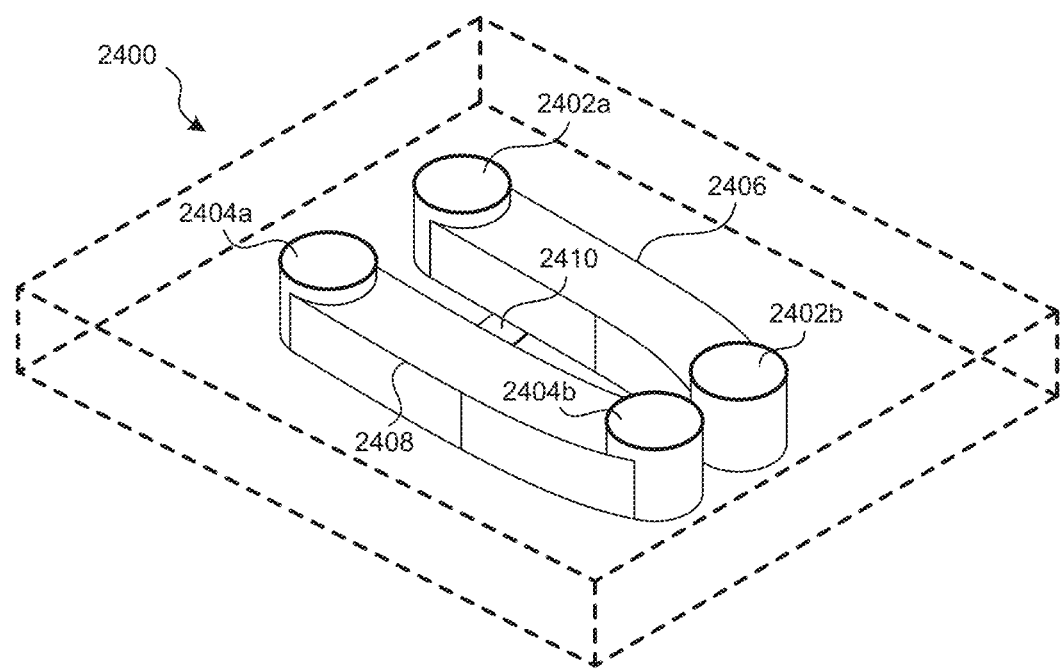
FIGS. 24A-24B illustrate a flow device for cell migration assays in accordance with select embodiments of the present technology.

Select embodiments of the present technology further provide flow devices for cell migration assays. For example, FIG. 24A is a negative space schematic illustration of a flow device 2400. Flow device 2400 can have a generally rectangular shape as illustrated by the dashed lines in FIG. 24A, although other shapes suitable for defining the negative space illustrated in FIG. 24A, including triangular, spherical or other shape suitable for defining the negative space illustrated in FIG. 24A. The device 2400 can have a bottom surface that can be placed in direct contact with an underlying substrate such as a glass slide or well plate. Thus, when placed on the substrate, the device can define a series of channels on the substrate, as described in detail below. To secure the device to the substrate, a hydrogel can be pipetted near an edge of the device 2400. The hydrogel can seep under the bottom surface of the device 2400 and act as a glue connecting the device 2400 and the substrate. In some embodiments, the hydrogel only flows under the portion of the device 2400 physically in contact with the substrate. Accordingly, the hydrogel does not flow into the negative space illustrated in FIG. 24A and described in detail below.

As illustrated, when flow device 2400 is placed on the substrate, flow device 2400 can define a first inlet port 2402a and a second inlet port 2404a at a proximal end portion of the device 2400. The first inlet port 2402a provides access to a first channel 2406 (e.g., a first bypass channel), and the second inlet port 2404a provides access to a second channel 2408 (e.g., a second bypass channel). In some embodiments, the device 2400 may further define a third inlet port 2402b that provides access to the first channel 2406 and is spaced apart from the first inlet port 2402a by a length of the first channel 2406, and a fourth inlet port 2404b that provides access to the second channel 2408 and is spaced apart from the second inlet port 2404b by a length of the second channel 2408. In some embodiments, the first and second channels 2406, 2408 can only be accessed via the first, second, third, and/or fourth ports 2402a, 2402b, 2404a, and/or 2404b. For example, in some embodiments the device 2400 may include a top surface that extends over the entirety of the negative space illustrated in FIG. 24A except for the inlet ports. The top surface can, for example, reduce the risk of contamination and enable assays to be performed in a more controlled environment. In some embodiments, the first channel 2406 and the second channel 2408 can extend distally from the proximal end region and can be generally parallel. The first and second channels 2406, 2408 can taper towards one another at second end regions distal the first and second inlet ports 2402, 2404.

The device 2400 can further define a migration channel 2410. The migration channel 2410 can connect the first channel 2406 and the second channel 2408. For example, the migration channel 2410 may fluidly couple the first channel 2406 and the second channel 2408. Thus, the first channel 2406 and the second channel 2408 can each have an intersection region near where the first and second channels are intersected by the migration channel. The migration channel 2410 and the intersection regions can facilitate cell migration between the first channel 2406 and the second channel 2408.

Figure 24B:
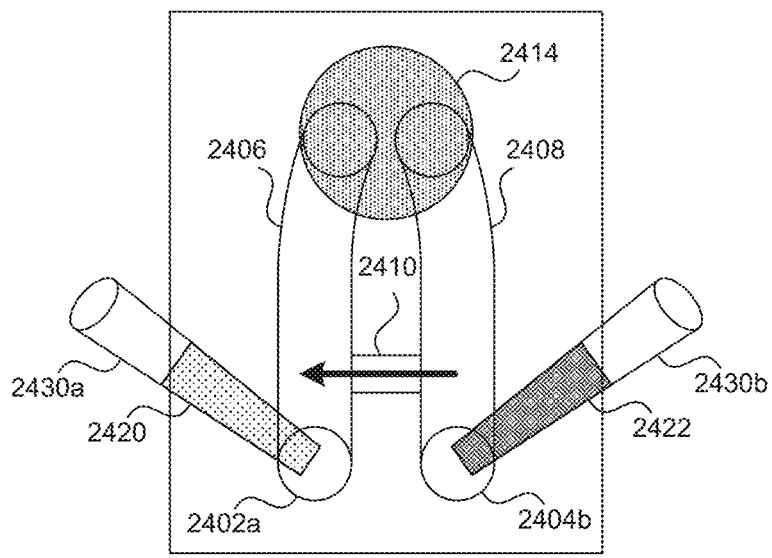

FIG. 24B illustrates a cell migration assay workflow using the flow device 2400. The flow device 2400 can be added to a substrate (e.g., a glass slide), and hydrogel can be used to glue the flow device 2400 to the substrate and prevent flowable materials from seeping underneath the base surface of the flow device 2400 in contact with the substrate. A chemoattractant 2420 can be added to the first port 2402 (e.g., via a first pipette 2430a) and cells 2422 can be added to the second port 2404 (e.g., via a second pipette 2430b). A bypass droplet 2414 can be added at the distal end region of the device 2400 at or near the third port 2402b and/or the fourth port 2404b to preferentially direct flow of the chemoattractant along the first channel 2406. This can reduce flow of the chemoattractant 2420 along the migration channel. The chemoattractant 2420 can create a gradient that causes cells 2422 to migrate from the second channel 2408 to the first channel 2406 via the migration channel 2410. Accordingly, in certain embodiments, the device 2400 can be used to perform cell migration assays.

Conclusion

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A spontaneous capillary flow device for patterning walls on a hydrophilic substrate, the device comprising:
   a rail, wherein the rail includes
      a first end portion including an inlet configured to receive a flowable material,
      a second end portion opposite the first end portion, and
      a base portion having a flow surface extending between the first end portion and the second end portion, wherein the flow surface is configured to define a flow path thereon; and
   one or more supports configured to space apart the flow surface and the hydrophilic substrate by a first distance such that the flow surface faces the hydrophilic substrate when spaced apart by the first distance;
   wherein, when the device is spaced apart from the hydrophilic substrate by the first distance and the flowable material is released into the inlet, the flowable material is configured to flow via spontaneous capillary flow from the first end portion to the second end portion along the flow path, and is configured to create a wall on the hydrophilic substrate, wherein the wall includes polymerized flowable material.

2. The device of claim 1 wherein the hydrophilic substrate is a bottom flow surface and the flow surface is a top flow surface, and wherein the device is configured to enable spontaneous capillary flow without additional flow surfaces.

3. The device of claim 1 wherein the device is configured to divide the hydrophilic substrate into two or more segregated zones separated by one or more walls.

4. The device of claim 1 wherein the inlet is a controlled inlet configured to direct the flowable material to a portion of the inlet adjacent to the flow surface.

5. The device of claim 1 wherein the second end portion includes a region having higher capillary favorability than the first end portion and the flow surface.

6. The device of claim 1 wherein the base portion of the rail has a first side and a second side, the first side and the second side extending from the flow surface, and wherein the base portion is configured to prevent capillary rise up the first side or the second side.

7. The device of claim 6 wherein the base portion has a substantially trapezoidal cross-section along a longitudinal length.

8. The device of claim 1 wherein the hydrophilic substrate is a base surface of a well, and wherein the device is positionable within the well.

9. The device of claim 8 wherein the one or more supports are pressure struts, and wherein the one or more pressure struts are configured to engage one or more side surfaces of the well to stabilize the device within the well.

10. The device of claim 1 wherein the one or more supports are feet, and wherein the individual feet are configured to contact the hydrophilic substrate at one or more positions outside of the flow path.

11. The device of claim 1 wherein the device is configured to create two or more segregated cell culture zones separated by one or more walls, and wherein the device further comprises a reservoir for retaining media and configured to mitigate the effects of evaporation from the two or more segregated cell culture zones.

12. The device of claim 11 wherein the reservoir extends at least partially around a periphery of the rail, and wherein the reservoir includes a pinning ridge dividing the reservoir from the rail.

13. The device of claim 1 wherein the hydrophilic substrate is a plastic or glass surface of a well plate, petri dish, glass slide, chemically modified well plate, chemically modified petri dish, or chemically modified glass slide.

14. The device of claim 1 wherein the hydrophilic substrate is a hydrogel layer.

15. The device of claim 14 wherein the hydrogel layer comprises cells.

16. The device of claim 1 wherein the flowable material includes cells.

17. The device of claim 1 wherein, after the wall is patterned on the hydrophilic substrate, the device can be removed from the wall such that the wall remains intact on the hydrophilic substrate.

18. The device of claim 1 wherein the device is manufactured via injection molding.

19. The device of claim 1 wherein the first distance is a height, and wherein the flow surface further comprises a width, and wherein the relationship between the height and the width are determinable based on:

$$\frac{h}{w} < \frac{\cos \theta_1 + \cos \theta_2}{2}$$

wherein h is the height, w is the width, $\theta_1$ is a contact angle of the device, and $\theta_2$ is a contact angle of the substrate.

* * * * *